(12) United States Patent
Bertolero et al.

(10) Patent No.: US 7,678,098 B2
(45) Date of Patent: Mar. 16, 2010

(54) VENOUS CANNULA AND CARDIOPULMONARY BYPASS SYSTEM

(75) Inventors: Raymond Bertolero, Danville, CA (US); Tamer Ibraham, Pleasant Hill, CA (US); Michael Torres, Tracy, CA (US)

(73) Assignee: Endoscopic Technologies, Inc., Danville, GA (US)

( * ) Notice: Subject to any disclaimer, the term of this patent is extended or adjusted under 35 U.S.C. 154(b) by 887 days.

(21) Appl. No.: 11/139,446

(22) Filed: May 27, 2005

(65) Prior Publication Data

US 2005/0222532 A1 Oct. 6, 2005

Related U.S. Application Data

(63) Continuation-in-part of application No. 10/996,876, filed on Nov. 23, 2004, which is a continuation of application No. 09/171,064, filed on Jun. 29, 1999, now Pat. No. 6,821,265, which is a continuation-in-part of application No. 08/766,384, filed on Dec. 6, 1996, now Pat. No. 5,868,703.

(60) Provisional application No. 60/014,922, filed on Apr. 10, 1996.

(51) Int. Cl.
*A61M 31/00* (2006.01)
(52) U.S. Cl. ...................... 604/500; 604/4.01
(58) Field of Classification Search ............... 604/4.01, 604/6.16, 93.01, 102.01, 102.03, 103.09, 604/264, 500
See application file for complete search history.

(56) References Cited

U.S. PATENT DOCUMENTS

| 4,129,129 | A | | 12/1978 | Amrine |
| 4,173,981 | A | | 11/1979 | Mortensen |
| 4,301,797 | A | | 11/1981 | Pollack |
| 4,639,252 | A | * | 1/1987 | Kelly et al. ................. 604/541 |
| 4,680,029 | A | | 7/1987 | Ranford et al. |
| 4,787,882 | A | | 11/1988 | Clarén |
| 4,804,365 | A | | 2/1989 | Litzie et al. |
| 4,808,163 | A | | 2/1989 | Laub |
| 4,863,441 | A | | 9/1989 | Lindsay et al. |
| 5,433,700 | A | | 7/1995 | Peters |
| 5,478,309 | A | * | 12/1995 | Sweezer et al. ............ 604/6.14 |
| 5,584,803 | A | | 12/1996 | Stevens et al. |
| 5,759,170 | A | | 6/1998 | Peters |
| 5,762,624 | A | | 6/1998 | Peters |

(Continued)

OTHER PUBLICATIONS

Medtronic Brochure Page, Carpentier Bi-Caval Femoral Venous Cannulae, p. 29 (one page only).

*Primary Examiner*—Nicholas D Lucchesi
*Assistant Examiner*—Christopher D Koharski
(74) *Attorney, Agent, or Firm*—Carol D. Titus; Gregory S. Smith; GSS Law Group

(57) ABSTRACT

This invention relates to a venous cannula for use in conjunction with cardiovascular examinations, treatments and surgery. The venous cannula is configured for two-stage drainage of oxygen-depleted venous blood from a central venous location via a peripheral venous insertion site, such as a femoral vein. The venous cannula is optimized for use in a cardiopulmonary bypass system that includes a multichannel arterial perfusion catheter. The cardiopulmonary bypass system is advantageous for use in performing standard open chest or least invasive cardiac surgical procedures.

10 Claims, 13 Drawing Sheets

U.S. PATENT DOCUMENTS

| | | |
|---|---|---|
| 5,769,828 A | 6/1998 | Jonkman |
| 5,823,986 A | 10/1998 | Peterson |
| 5,863,366 A | 1/1999 | Snow |
| 5,957,879 A | 9/1999 | Roberts et al. |
| 6,042,576 A | 3/2000 | DeVries |
| 6,056,723 A | 5/2000 | Donlon |
| 6,182,664 B1 | 2/2001 | Cosgrove |
| 6,443,922 B1 | 9/2002 | Roberts et al. |

* cited by examiner

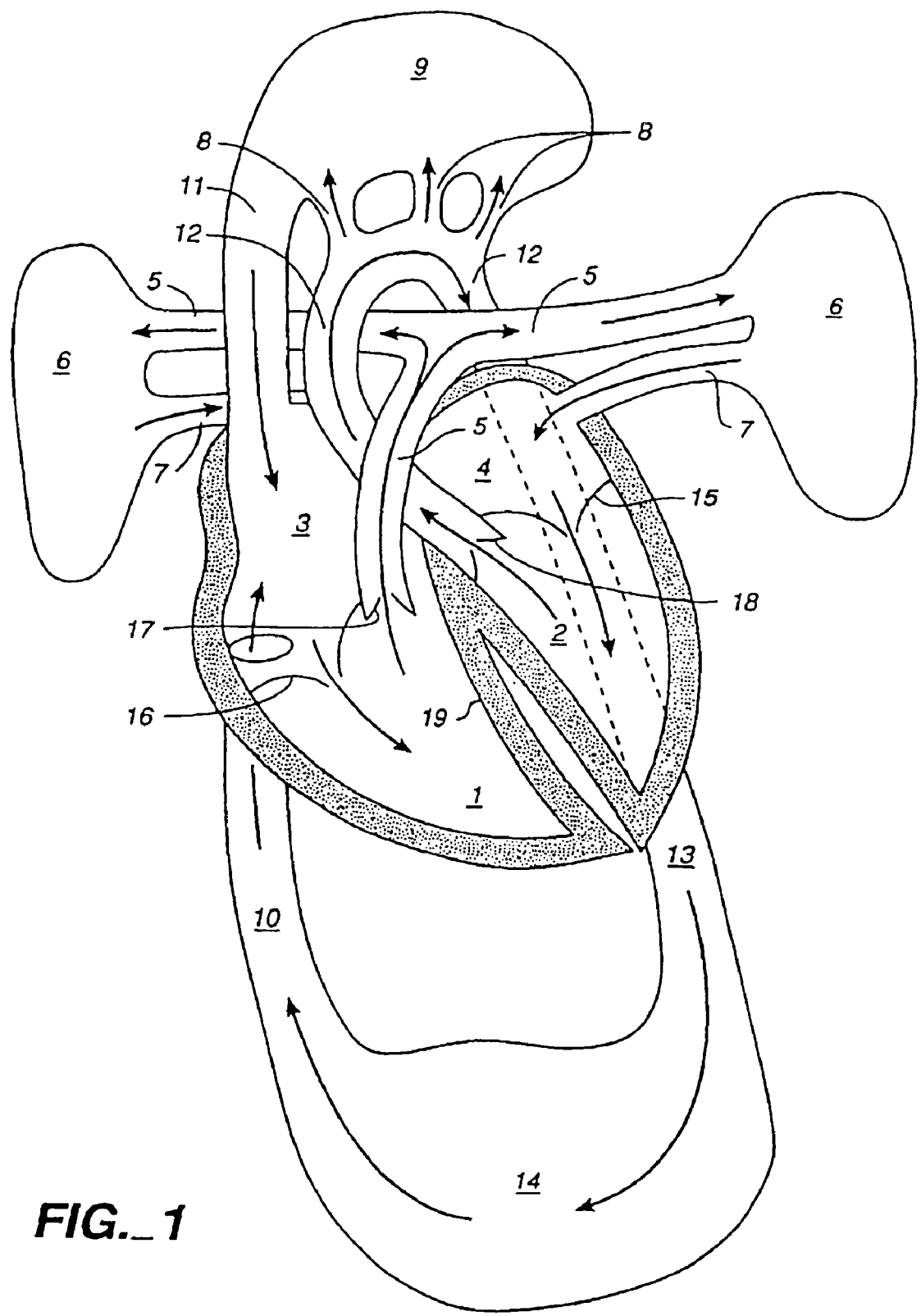
FIG._1

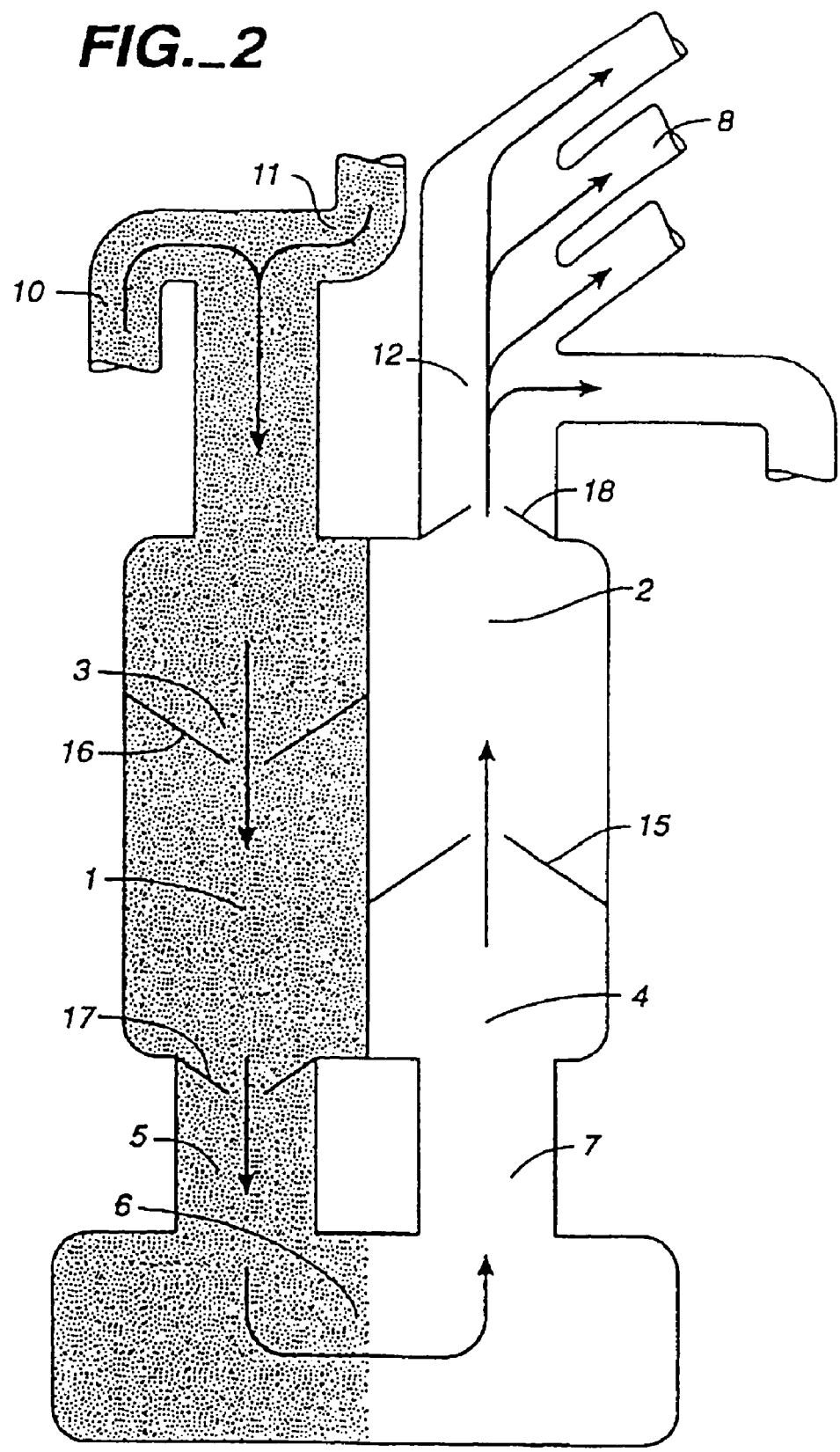
FIG._2

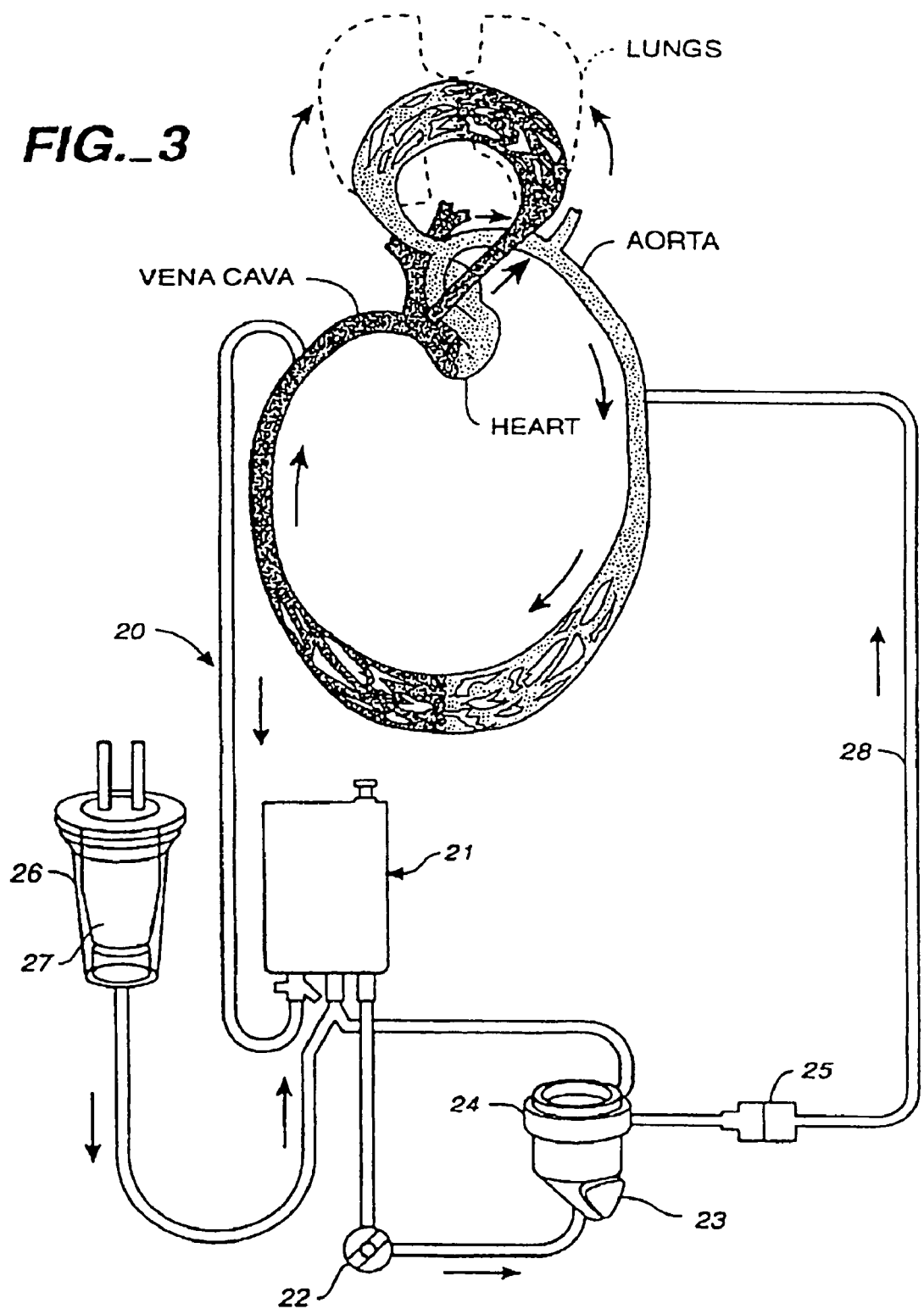
FIG._3

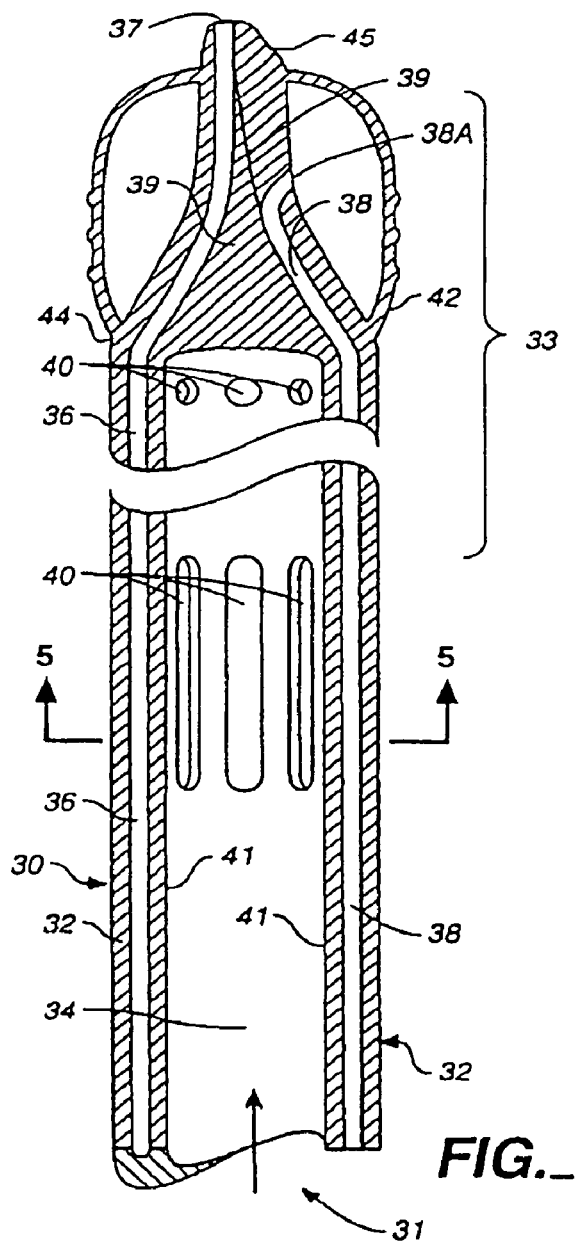
FIG._4
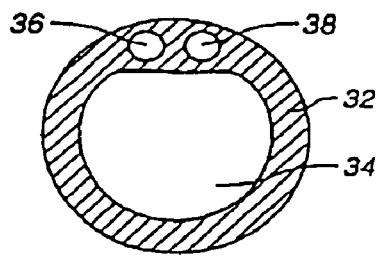
FIG._6
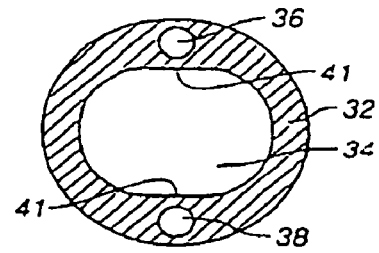
FIG._5A
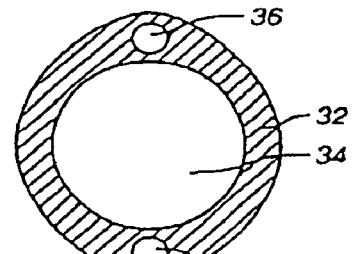
FIG._5B
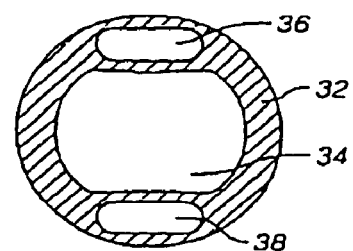
FIG._5C
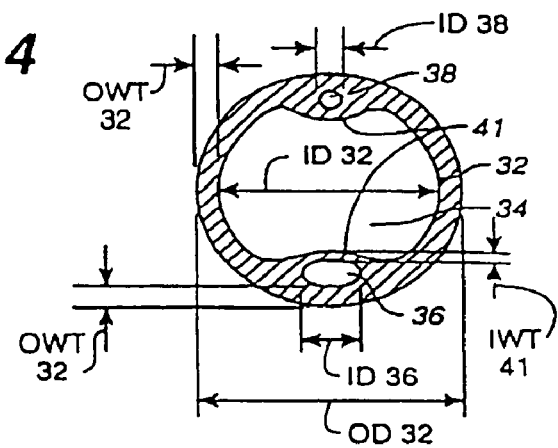
FIG._7

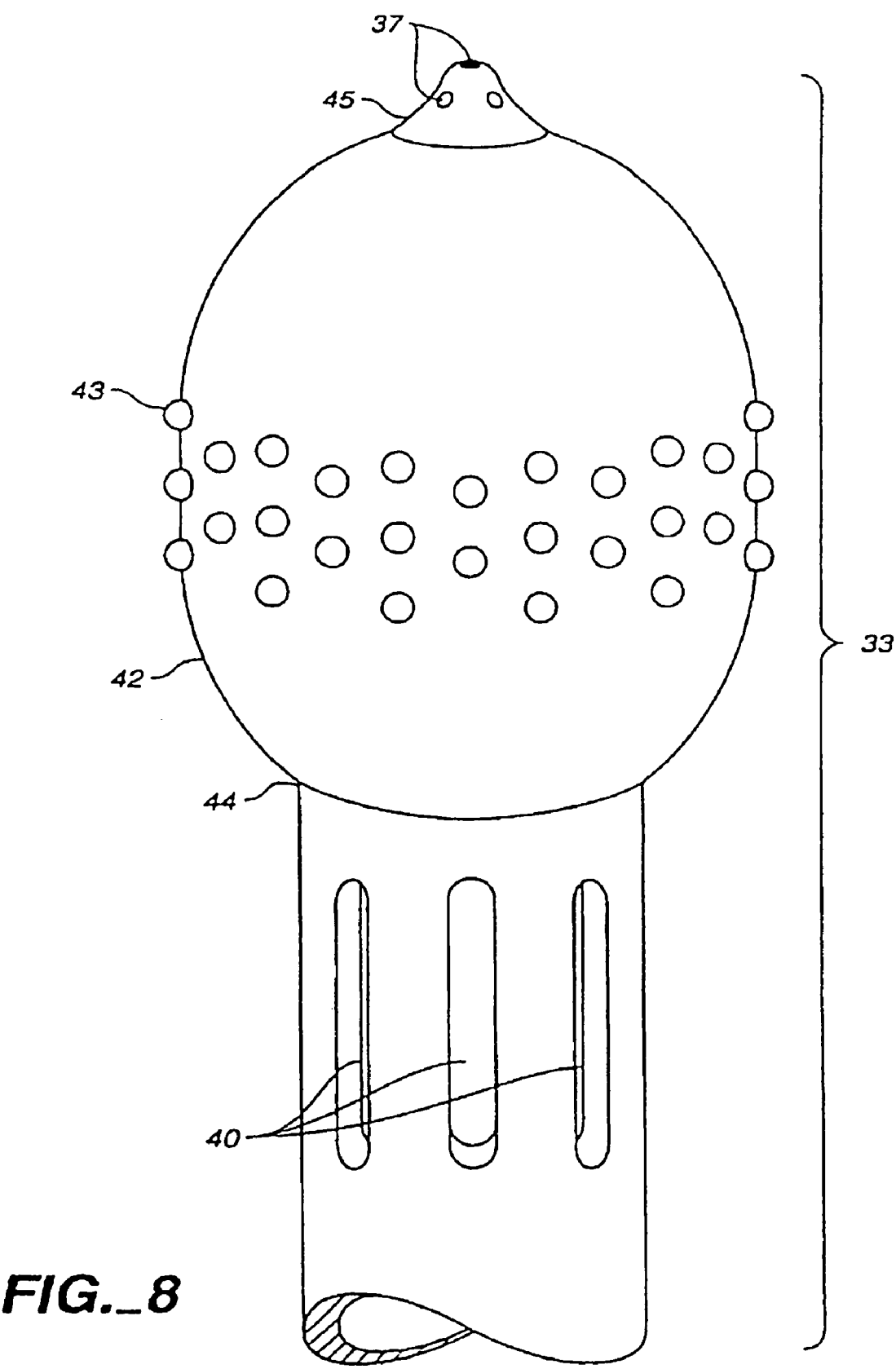
FIG._8

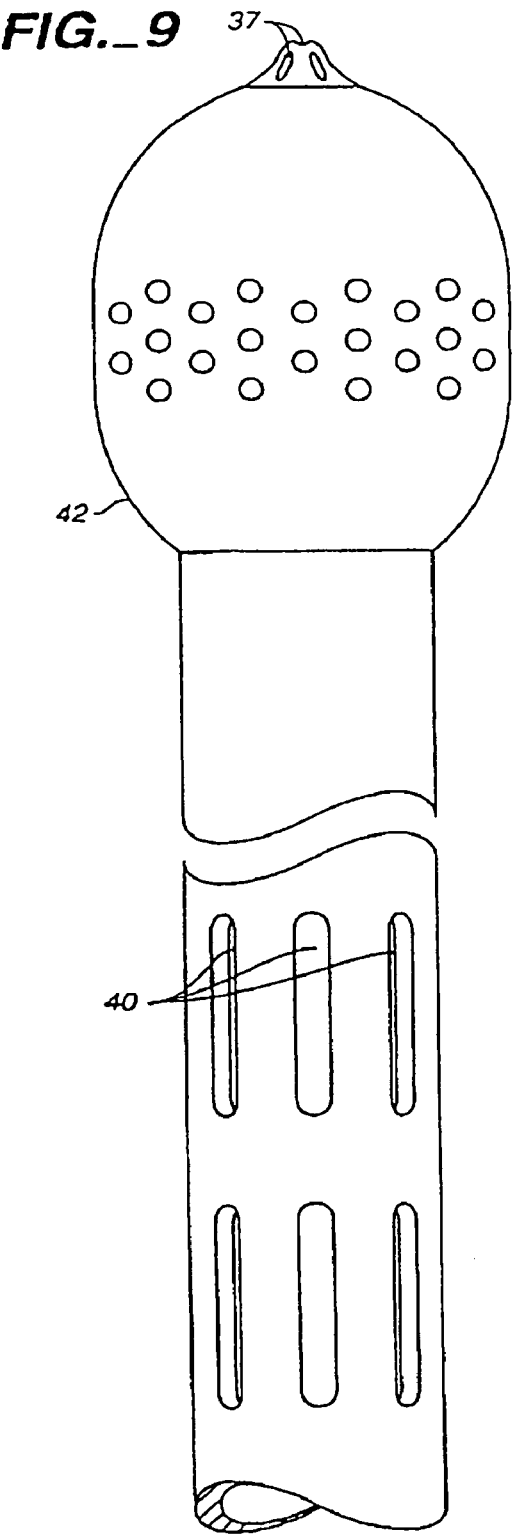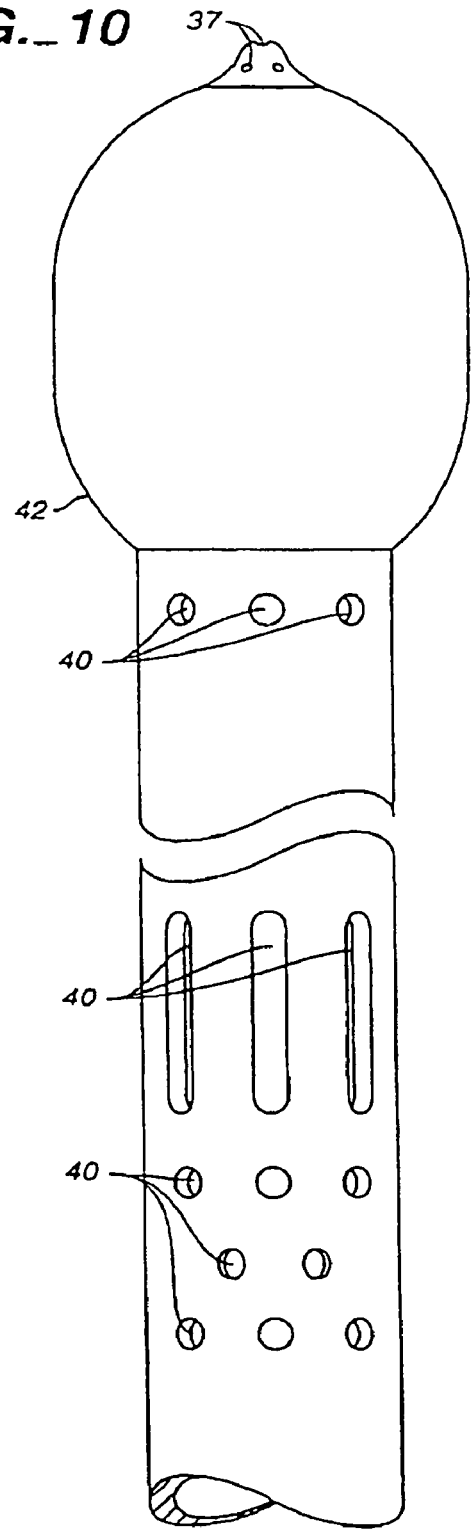

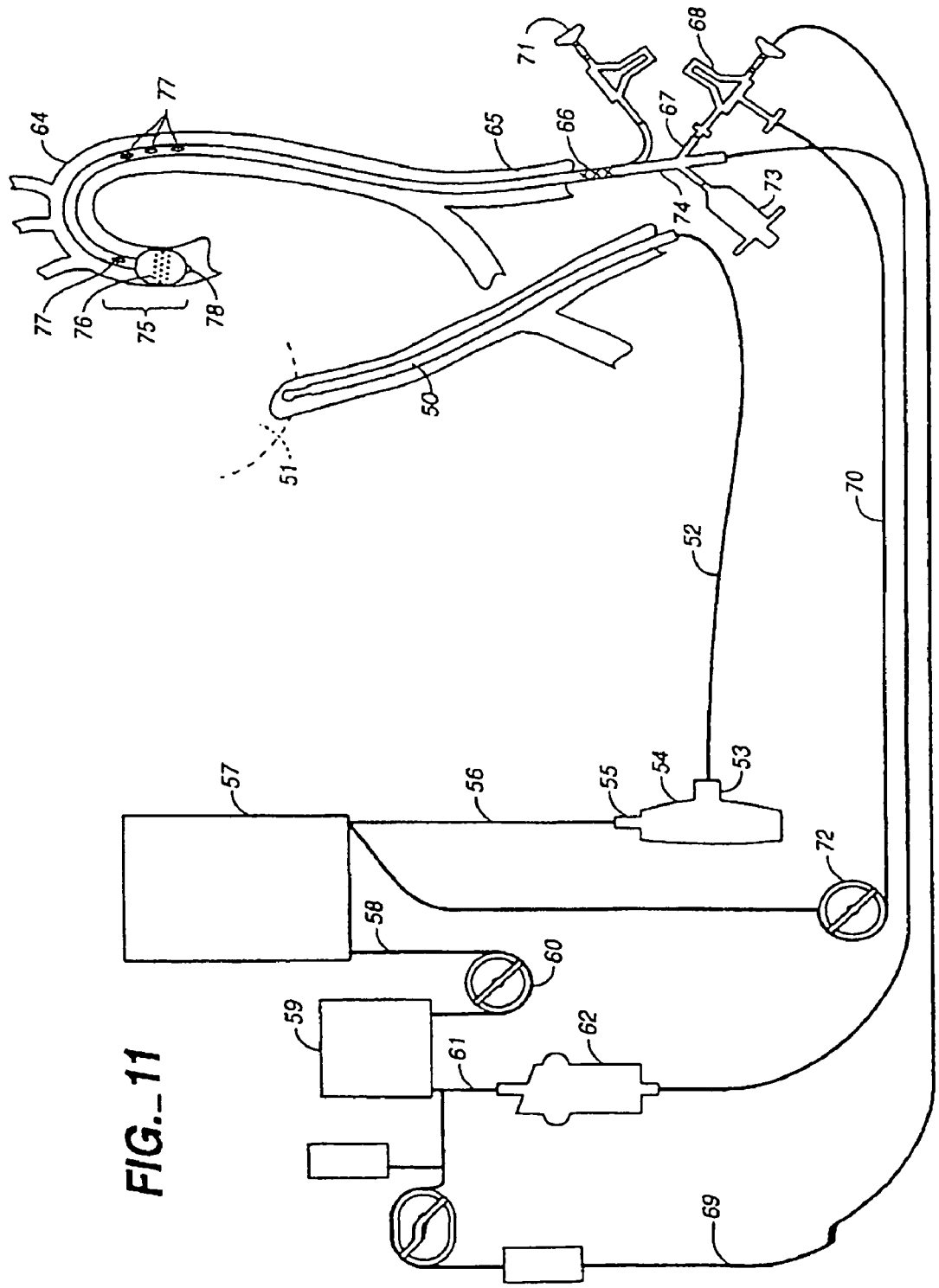
FIG._11

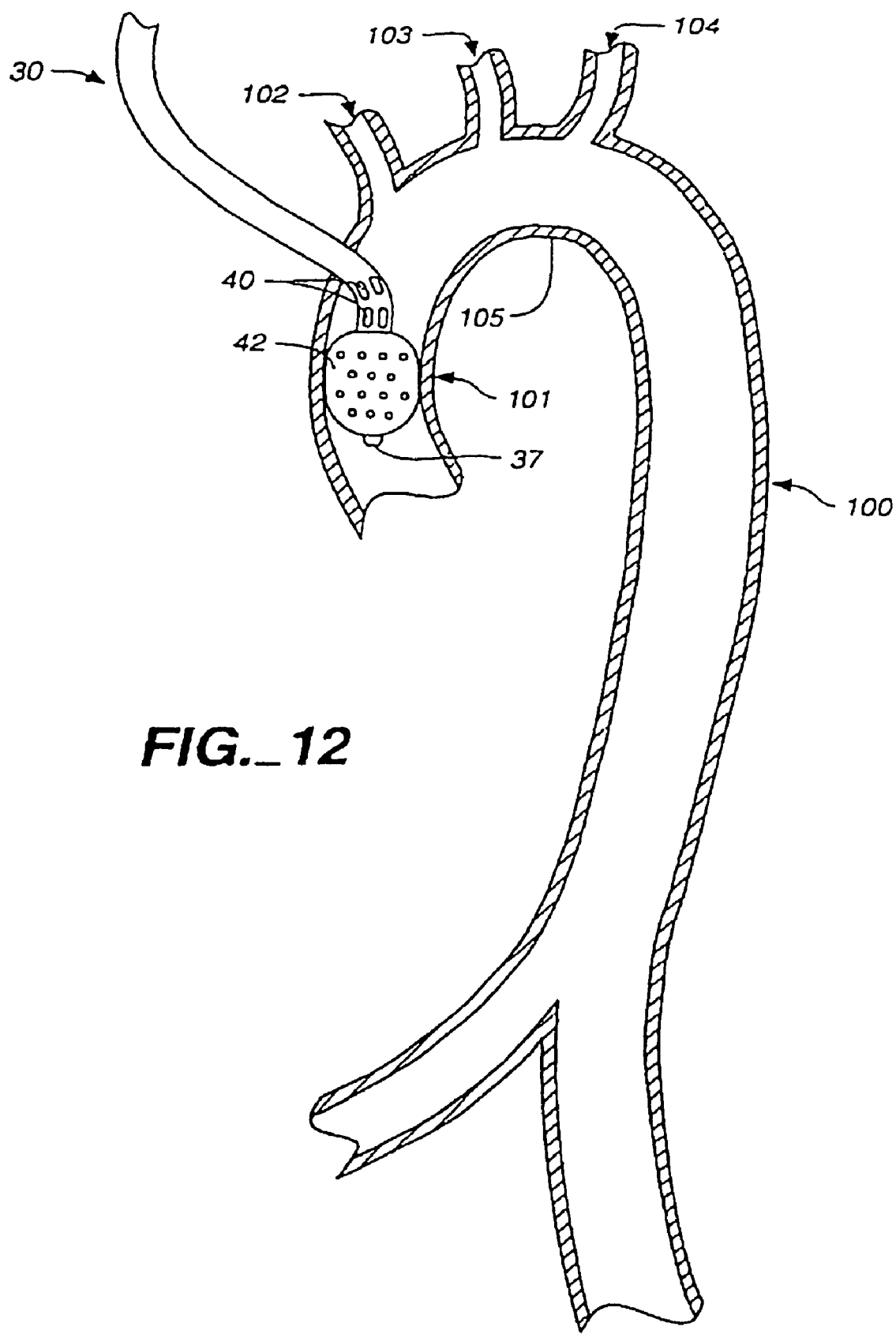
FIG._12

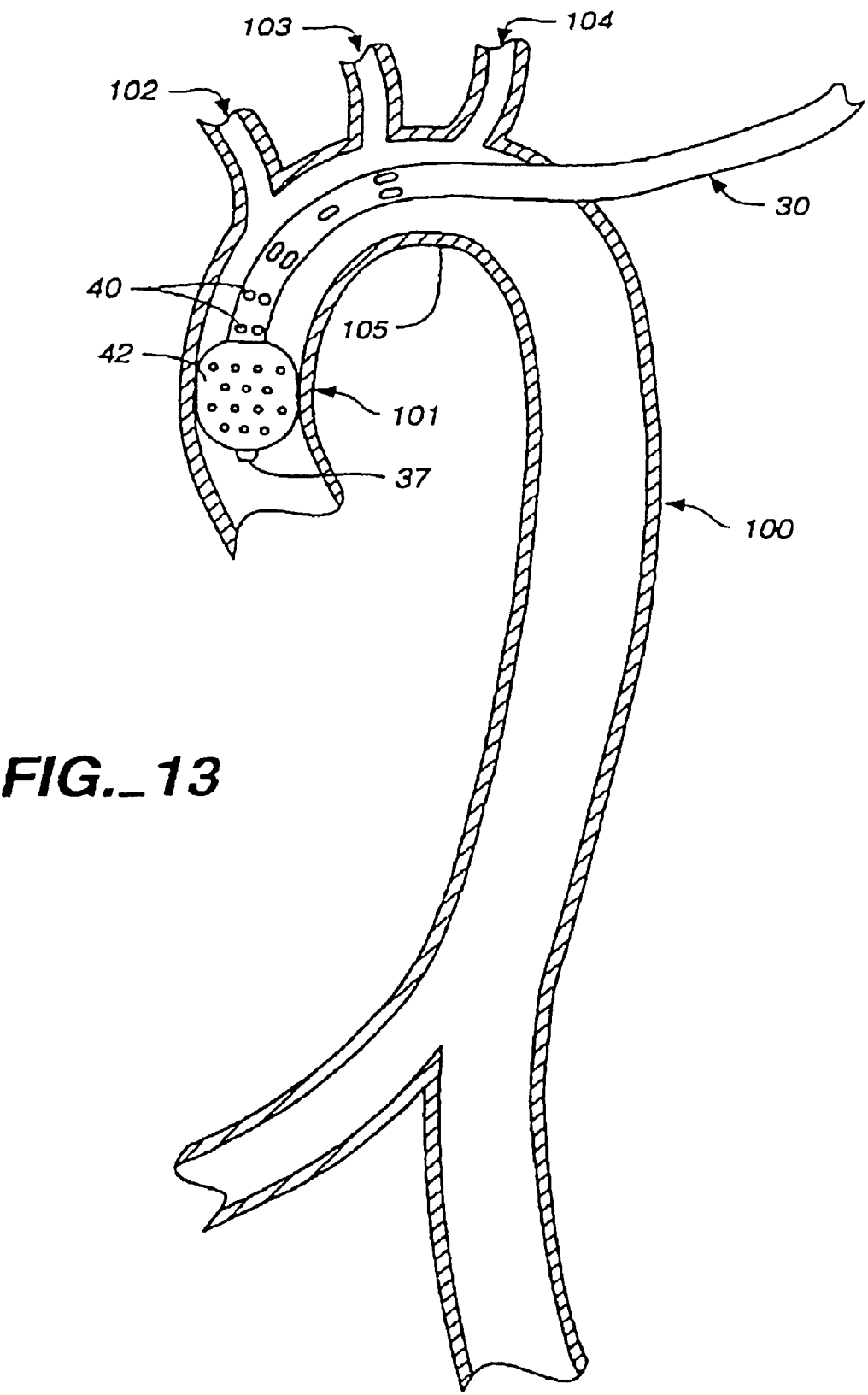
FIG._13

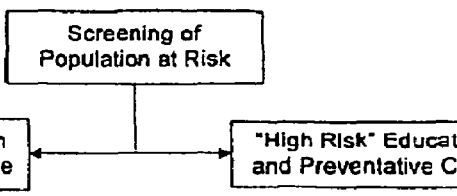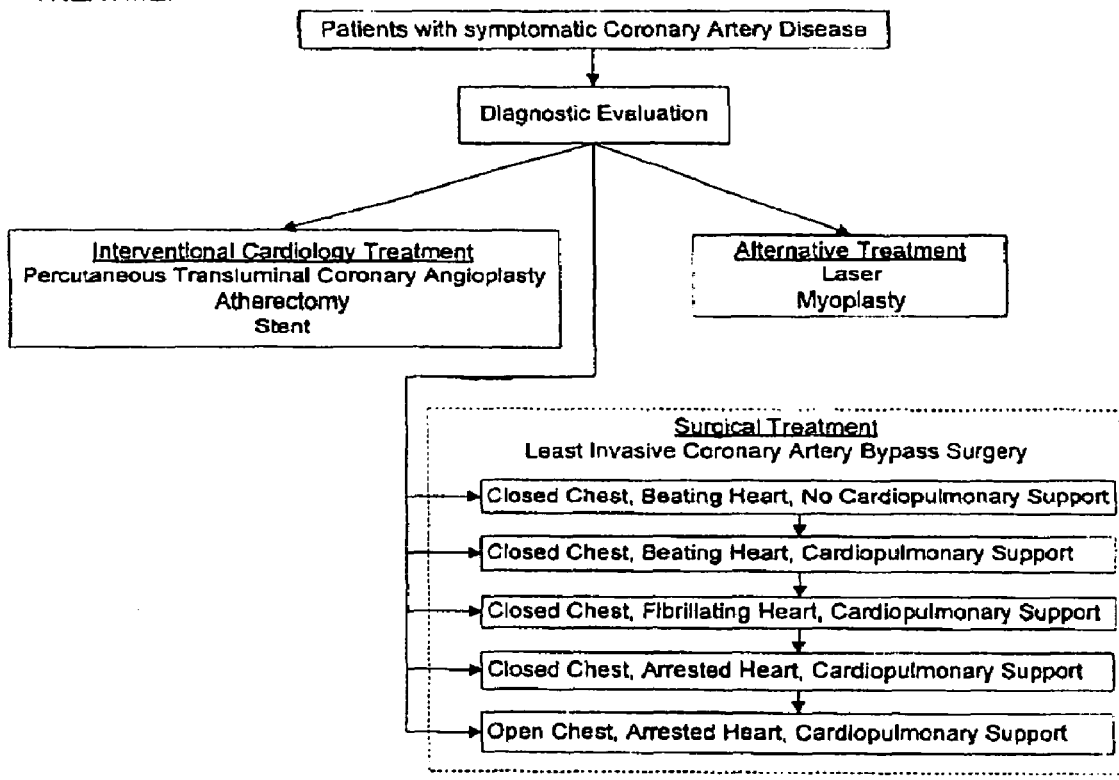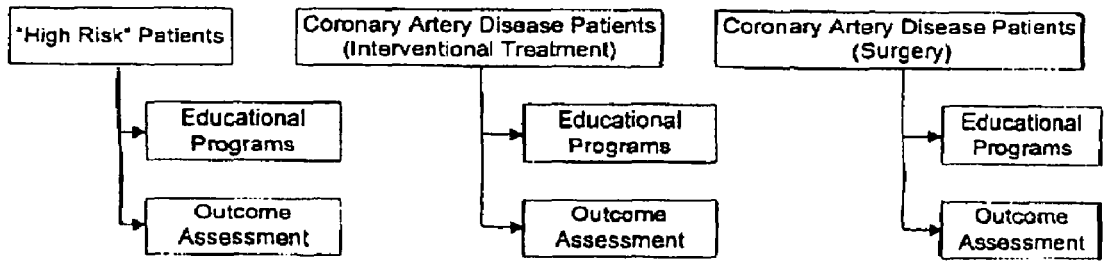
FIG._14

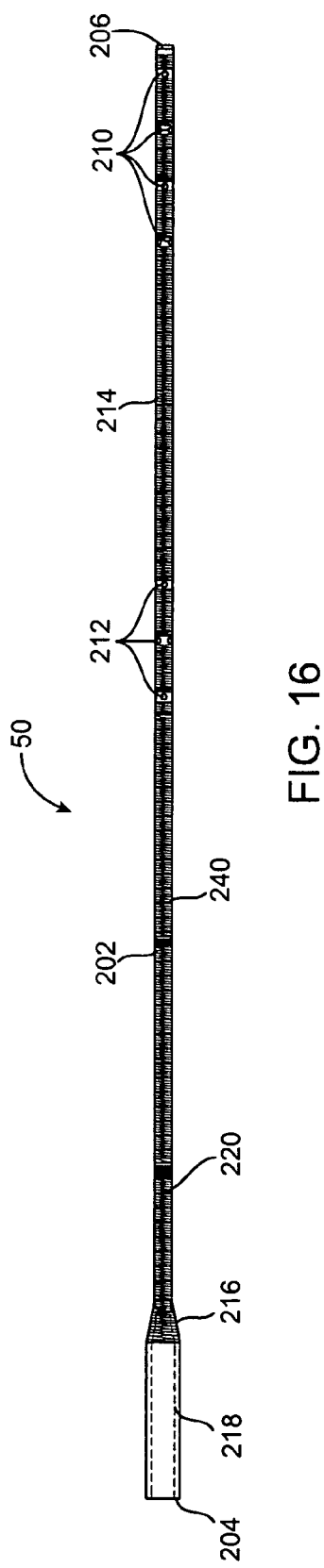
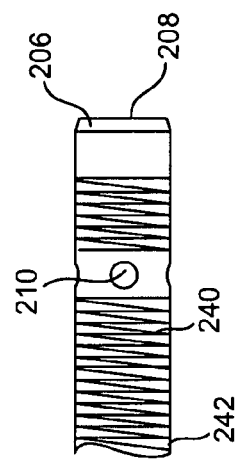
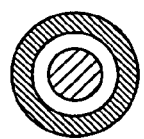
FIG. 16
FIG. 17
FIG. 18

VENOUS CANNULA AND CARDIOPULMONARY BYPASS SYSTEM

CROSS-REFERENCE TO OTHER APPLICATIONS

This application is a continuation-in-part of U.S. patent application Ser. No. 10/996,876 filed Nov. 23, 2004, which is a continuation of U.S. patent application Ser. No. 09/171,064 filed Jun. 29, 1999, now U.S. Pat. No. 6,821,265, which is a continuation-in-part of U.S. patent application Ser. No. 08/766,384 filed Dec. 6, 1996, now U.S. Pat. No. 5,868,703, which claims the benefit provisional application U.S. Application No. 60/014,922, filed 10 Apr. 1996.

FIELD OF THE INVENTION

This invention relates to a venous cannula and a cardiopulmonary bypass system for use in conjunction with cardiovascular examinations, treatments and surgery. It also relates to methods for performing cardiopulmonary bypass using the venous cannula and a multichannel arterial perfusion catheter.

BACKGROUND OF THE INVENTION

To better understand the background and problems faced by those of skill in this area of technology it is useful to understand the basic workings of the heart and circulatory system. The following discussion refers to schematics of the heart shown in FIGS. 1 and 2.

The human heart is a muscular pump having four separate cavities and a series of valves allowing blood to pass in one direction only. Mammals, including humans, have a double circulatory system. Blood that has released oxygen to the tissues (9 and 14) and has absorbed carbon dioxide from them (venous blood) is returned to the heart through the superior and the inferior venae cavae (11 and 10). This blood enters the right auricle (3), whose contractions cause the blood to pass through the tricuspid valve (16) in the right ventricle (1). The contractions of the right ventricle pass the blood through the pulmonary semilunar valves (17) and along the two pulmonary arteries (5) into the lungs (6). In the lungs, the blood is oxygenated and returns to the heart through the pulmonary veins (7) and thus enters the left auricle (4). This chamber contracts and passes the blood through the bicuspid, or mitral, valve (15) into the left ventricle (2), whose contractions force the blood through the aortic semilunar valve (18) into the aorta (12 and 13), which is the biggest artery of the body and to other parts of the body through, i.a., the great arteries 8.

Thus the right side of the heart serves mainly to pump deoxygenated blood through the lungs, while the left side pumps oxygenated blood throughout the rest of the body. This is represented as a flow schematic in FIG. 2, where similar numbers refer to similar parts of the heart. The heart varies the output by varying the volume of blood admitted into the ventricles each time the latter are filled and also by varying the rate of contraction (faster or slower heartbeat). The left side of the heart (left auricle and ventricle) has to circulate the blood through all parts of the body, except the lungs, and has thicker and more strongly muscular walls than the right side, which has to perform the pulmonary blood circulation only. For proper functioning, the left side and the right side must be accurately interadjusted, both with regard to the contraction rate of the respective chambers and with regard to the output of blood. When functional disorders of the heart occur, it may be necessary to examine the heart to determine the problem and possibly perform surgery or provide treatment.

In performing examinations or treatments of a subject's heart, or performing surgery on the heart, it is often necessary to reduce the rate at which it normally beats or stop its beating completely. This allows a physician to observe, or operate on, the heart more easily. However, by reducing or stopping the heart rate (i.e. cardioplegia), blood will not be adequately circulated to the rest of the body. Thus, it is generally necessary to circulate the blood using some type of extracorporeal blood circulating means that regularly circulates oxygen-rich blood through the arteries, collects oxygen-depleted blood returning through the veins, enriches the oxygen-depleted blood with additional oxygen, then again circulates the oxygen-rich blood.

The types of examinations, treatments and operations that require some degree of cardioplegia or drug delivery and extracorporeal blood circulation include open heart surgery and less-invasive heart surgery to perform single or multiple coronary artery bypass operations, correct malfunctioning valves, etc. Others include, but are not limited to, myocardial revascularization, balloon angioplasty, correction of congenital defects, surgery of the thoracic aorta and great vessels, and neurosurgical procedures.

The extracorporeal blood circulation generally requires the use of some type of heart-lung machine, i.e. a cardiopulmonary machine. This has the threefold function of keeping the replacement blood in circulation by means of a pumping system, of enriching with fresh oxygen the blood of low oxygen content coming from the patient's body, and regulation of patient temperature. The system shown in FIG. 3 diagrammatically describes the manner in which such a machine works.

The venous blood, before it enters the right auricle of the heart is diverted into plastic tubes (20), generally by gravity flow. The tubes are positioned to receive the blood from the superior and inferior venae cavae (shown as 11 and 10 in FIG. 1). This blood, which has circulated through the body and consequently has a low oxygen content is collected in a reservoir (21). A blood pump (22) is used to pump the blood through a heat exchanger (23) and artificial lung (24). The heat exchanger (23) and artificial lung (24) may be one of several designs to regulate blood temperature and increase the oxygen content of the blood. Modern designs use advanced membrane technology to achieve the oxygenation, which is similar to the way red blood cells absorb oxygen from the human lung. The oxygenated blood then passes through a filter (25) and is returned to the patient. Losses of blood occurring during the course of the operation are compensated by an additional blood reservoir (26). Collected blood is passed through a defoamer (27) and is likewise passed to the to the reservoir 21, heat exchanger (23) and artificial lung (24). Before starting the cardiopulmonary bypass machine the extracorporeal circuit is filled with one or two liters of saline solution.

In circulating the oxygenated blood to the body from filter 25, it can be pumped through a catheter 28 by inserting the catheter into the aorta or one of its major branches and pumping the blood through the catheter. However, when the heart is to be operated on, it must be free of blood and sometimes the heart beat must be reduced or stopped completely. Referring again to FIG. 1, blood is prevented from entering the heart by blocking the ascending aorta 12 near the semilunar valve 18 while at the same time preventing blood from entering the right auricle 3 by withdrawing blood through the superior vena cavae 11 and inferior vena cavae and 10. Blocking the ascending aorta may be achieved by clamping or preferably by balloon blockage. At the same time that blood is prevented from flowing through the heart, a cardioplegia solution is administered locally to the heart to arrest the heart. Thus, there is a need for a device that allows a heart specialist to locally administer cardioplegia to the heart, block the flow of blood to the heart, while at the same time circulating oxygenated blood to the patient's body, particularly through the great arteries (8 in FIG. 1), to ensure all limbs and tissues remain undamaged during the heart examination or operation.

Several devices are described in the literature to address the need for an appropriate device. One example is disclosed in U.S. Pat. No. 5,312,344 issued 17 May 1994 to Grinfeld et al. This patent describes a multichannel catheter having at least three passageways, one of which is used for blood circulation and another is used for cardioplegia transportation. The third is used to transport fluid to an inflatable balloon which is located at the distal end of the catheter and is used to block the ascending aorta. The channel for blood is described as having outlets on the downstream side of the balloon to allow blood to be circulated to the body tissues. The design of this multichannel catheter shows that either each passageway is a tube encased in a cannula or the smaller passageways are located within the larger passageway for cardioplegia solution or blood. Thus, the small passageways are not integral with the walls of the blood-carrying tube. Also, there is no teaching of the importance of the large volume needed for the blood-carrying catheter.

Another example can be seen in U.S. Pat. No. 5,433,700 issued 18 Jul. 1995 to Peters. This patent describes a process for inducing cardioplegic arrest of a heart which comprises maintaining the patient's systemic circulation by peripheral cardiopulmonary bypass, occluding the ascending aorta through a percutaneously placed arterial balloon catheter, venting the left side of the heart, and introducing a cardioplegia agent into the coronary circulation. As part of the disclosure a multichannel catheter is disclosed which provides channels for the cardioplegia solution, a fluid transportation to inflate the balloon and a lumina for instrumentation. However, there is no description in the patent of a multichannel catheter which is designed to administer cardioplegia solution, inflate a balloon, and provide circulation of blood all using the same multichannel catheter. The Peters process teaches the use of a separate catheter to deliver oxygenated blood to the body while a heart is stopped.

Another example of a device is found in U.S. Pat. No. 5,478,309 issued 26 Dec. 1995 to Sweezer et al. This is a rather complex device and system of venous perfusion and arterial perfusion catheters for use in obtaining total cardiopulmonary bypass support and isolation of the heart during the performance of heart surgery. One of the multichannel catheters described in the patent for delivering cardioplegia solution to the heart while blocking the ascending aorta and circulating perfused blood. This catheter requires a cannula having two passageways therethrough. In the first passageway another slidable cannula having two passageways through it and having a passageways for guidewires are positioned. These passageways are for delivering a fluid for inflating the balloon at the distal end of the catheter and cardioplegia solution to the heart to stop its beating. The second passageway through the cannula used for transporting blood that has been oxygenated by the cardiopulmonary machine. However in this particular design no discussion of the need to maximize the flow of blood and minimize the damage to the blood components is discussed. Thus the volume of the two passageways is about the same.

Another device is described in U.S. Pat. No. 5,458,574 issued 17 Oct. 1995 to Machold et al. It shows a multichannel catheter which has channels for fluid to blow up balloons for blocking the aorta, a channel for cardioplegia solution and a channel for instruments for examining the heart. Nothing in the patent describes a multichannel catheter of applicant's design.

Still another patent, U.S. Pat. No. 5,452,733 issued 26 Sep. 1995 to Sterman et al. No details are given in that patent of the design of the catheter that might be used.

Still another patent application filed as PCT/US 94/09938 having international publication No. WO95/08364 filed 1 Sep. 1994 in the name of Evard et al. describes an endovascular system for arresting the heart. This too lacks any detailed description of a multichannel catheter that could be used in the manner described in the instant application.

PCT International Application number PCT/U.S. No. 94/12986 published as Publication No. WO95/15192, filed 10 Nov. 1994 in the name of Stevens et al. provides a description of a partitioning device that is coupled to an arterial bypass cannula. The description provides for the cannula to be introduced to the femoral artery where the partitioning device has a balloon at the end of the flexible tube to block the ascending aortic artery and allow blood to circulate through a lumen.

While the above devices address in part the needs of the art, it has been discovered that certain problems exist that must be further addressed to maximize the efficiency of the device and cardiopulmonary operations. The first problem is ensuring maximum flow of blood through the device (which must be of a diameter sufficiently small to fit into a patient's femoral artery) so that the tissues receive enough nourishment (i.e. oxygen, etc.). We have found that by ensuring that (1) the channel for blood is at least 70% of the available volume and (2) the channel for blood is clear of an other tubes or obstructions, the blood flow is maximized. Another problem is ensuring that the blood components are not injured by excess flow rate and sheer stress in the circulation process. We have found that by providing strategically located blood outlets that are preferably elongate in shape the sheer stress is reduced. Another problem is ensuring the blood flow to the great arteries is maximized to avoid damage to the tissues, particularly the brain. We have found tissue damage is avoided by ensuring the blood circulating outlets are located on the catheter such that when the catheter of this invention is in place, the outlets are located adjacent to the great artery openings. Finally we have found that by using extrusion molding techniques the multichannel catheter of this invention is prepared so that (1) the blood-carrying passageway is at least about 70% of the available volume and (2) the other passages account for less than about 30% of the available volume and are integral with the wall of the blood-carrying passageway, the blood flow problems are minimized.

U.S. Pat. No. 6,837,854 to Bertolero et al describes a Multichannel Catheter with Obturator that can be used in conjunction with the venous cannula and cardiopulmonary bypass system of the present invention. This and all patents and patent applications referred to herein are incorporated by reference in their entirety.

OBJECTS OF THE INVENTION

An object of this invention is to provide an improved venous cannula for use in a cardiopulmonary bypass system.

Another object of this invention is to provide a venous cannula that is optimized to provide improved efficiency in a cardiopulmonary bypass system using a multichannel arterial perfusion catheter.

Another object of this invention is to provide an improved process for performing surgery on a mammal's heart.

Another object of this invention is to provide a venous cannula and cardiopulmonary bypass system that are useful in both open chest and least invasive heart surgery.

It is another object of this invention to provide improvements in the management and treatment of coronary heart disease.

SUMMARY OF THE INVENTION

One aspect of this invention is a venous cannula for use in conjunction with cardiovascular examinations, treatments and surgery. The venous cannula is configured for two-stage drainage of oxygen-depleted venous blood from a central venous location via a peripheral venous insertion site, such as a femoral vein. The venous cannula is optimized for use in a cardiopulmonary bypass system that includes a multichannel arterial perfusion catheter. The cardiopulmonary bypass system is advantageous for use in performing standard open chest or least invasive cardiac surgical procedures.

The venous cannula has an elongated, coil wire reinforced, tubular body with a central lumen extending through it. The venous cannula body has an open distal end hole and a plurality of side ports that are configured to optimize blood flow through the central lumen. The side ports are divided into distal side ports, which are grouped together on a distal portion of the venous cannula body for withdrawing blood from the patient's right auricle and/or superior vena cava, and proximal side ports, which are grouped together on a proximal portion of the venous cannula body for withdrawing from the patient's inferior vena cava. An imperforate section of the venous cannula body separates the distal side ports from the proximal side ports. A proximal connector attached to the proximal end of the venous cannula body is configured for attachment to the inlet of cardiopulmonary bypass system with a minimum of head loss.

The venous cannula includes a dilator/obturator that can be inserted into the central lumen of the venous cannula to prevent flow of blood through the central lumen during introduction of the venous cannula. The dilator/obturator has a tapered distal portion to facilitate insertion of the dilator/obturator and the venous cannula into a vein at the peripheral venous access site.

Another aspect of this invention is a single, multichannel catheter useful for extracorporeal circulation of blood to a patient undergoing cardiovascular treatments or surgery. The catheter has three independent channels and an expandable balloon at one end of the catheter. The first channel is the largest and is of a size that allows for delivery of blood to a patient in an amount sufficient to maintain the patient's metabolism and perfusion throughout the treatment or surgery. A second channel, smaller than the first, is integrated into the wall of the first channel and is suitable for delivering cardioplegia fluid to the heart and/or venting the left heart. A third channel, also smaller than the first, is integrated into the wall of the first channel and suitable for delivering a fluid to the balloon for its expansion when positioned in the ascending aorta to occlude the flow of blood to the heart.

Another aspect of this invention may be viewed as an improved method of performing cardiovascular surgery on a patient using a cardiopulmonary machine for extracorporeal circulation of blood. The improvement comprises using the catheter of this invention to deliver blood to the patient, provide cardioplegia fluid to the heart, occlude the flow of blood to the heart, and vent the heart if needed.

Another aspect of this invention is the multichannel catheter wherein the large first channel (i) extends substantially the length of the catheter, (ii) comprises at least about seventy percent of the available channel volume of the catheter, (iii) is defined by the wall of the catheter, and (iv) has its distal end in fluid communication with the expandable balloon. The second channel (i) extends substantially the length of the catheter parallel to said first channel but independent thereof, (ii) is integrated into the wall of the first channel, and (iii) is open at its distal end. The third channel extends substantially the length of the catheter parallel to the first and second channels but independent thereof. The third channel comprises, in combination with the second channel, not more than about thirty percent of the available channel volume of the catheter, is integrated into the wall of the first channel and spaced from the second channel, and is closed at its distal end. In the wall of the catheter near the distal end of the catheter and communicating with said first channel are a plurality of openings. The balloon means is integrated into the distal end of the catheter downstream from the first channel openings but upstream of the second channel distal opening and communicates with the third channel through an opening in the wall of the catheter. The catheter is of a size suitable for insertion into a blood vessel of a mammal and is for use in conjunction with cardiovascular examinations and surgery. Preferably the plurality of openings communicating with the first channel are elongate with the length of the openings being parallel to the length of the catheter and the first channel is large enough to transport oxygenated blood there through from the proximal end to the distal end.

Another aspect of this invention is a process of preparing the precursor to the multichannel catheter described herein, which process comprises (A) Extrusion molding a catheter having distal and proximal ends wherein the catheter comprises: (1) a central, first channel (a) extending substantially the length of the catheter, (b) comprising at least about seventy percent of the available channel volume of the catheter, and (c) being defined by the wall of the catheter; (2) a second channel (a) extending substantially the length of the catheter parallel to said first channel but independent thereof and (b) being integrated into the wall of the first channel; (3) a third channel (a) extending substantially the length of said catheter parallel to the first and second channels but independent thereof, (b) comprising, in combination with the second channel, not more than about thirty percent of the available channel volume of the catheter, and (c) being integrated into the wall of the first channel and spaced from the second channel. Other steps are taken to complete the catheter, as discussed hereinafter.

Another aspect of this invention is a process for providing oxygen-rich blood to a subject's arterial circulation and providing cardioplegia solution to the heart of the subject to arrest the heart and minimize damage to the heart. The process comprises: positioning the multichannel catheter, as described hereinbefore, in the ascending aorta; providing a source of oxygen-rich blood to the proximal end of the first channel of the catheter; providing a source of cardioplegia fluid to the proximal end of the second channel of the catheter; providing a source of fluid for inflating the inflatable means to the proximal end of the third channel of the catheter; positioning the multichannel catheter within the subject's blood circulatory system such that (a) the distal end of said catheter is positioned in the ascending aorta and the first channel openings are located proximate the great arteries, (b) the inflatable means is located on the cephalid side of the aortic valve, and (c) the distal end of the second channel is located proximate the aortic valve and downstream of the inflatable means; inflating the inflatable means to block the flow of blood to the heart; pumping cardioplegia solution into the heart to arrest the subject's heart rate; pumping oxygen-rich blood through said first channel out the first channel openings at rate sufficient to maintain the subject's metabolism and perfusion; performing a surgical operation on the heart as needed; and maintaining circulatory support of said subject as needed.

Other aspects of the invention will be apparent to one of skill in the art upon further reading the following specification and claims.

BRIEF DESCRIPTION OF THE DRAWINGS

FIG. 1 is a diagram of a mammal's heart and circulatory system showing the approximate configuration of the heart.

FIG. 2 is a schematic representative of how a mammalian heart works without regard to its configuration.

FIG. 3 is a schematic representation of how a cardiopulmonary machine works.

FIG. 4 is a longitudinal cross-section view of a multichannel catheter of this invention showing the interrelationship between the major portions of the invention.

FIG. 5A is a perpendicular cross-section taken along lines 5-5 of the longitudinal axis of the device of this invention shown in 4A.

FIG. 5B shows a closely related configuration taken along line 5-5 of FIG. 4a.

FIG. 5C shows a slight modification of the cross-section taken along the line of 5-5 of FIG. 4.

FIG. 6 shows a cross-section of the longitudinal axis of a slightly different configuration of the multichannel catheter of this invention.

FIG. 7 shows a perpendicular cross-section taken along lines 5-5 of FIG. 4 and shows the size relationships between the various parts of the multi-channel catheter of this invention.

FIG. 8 is a perspective closeup of the distal end of the catheter of this invention showing an inflated balloon and elongate openings.

FIG. 9 is a side elevation closeup of the distal end of the catheter of this invention showing an alternative design for the elongate openings.

FIG. 10 is a side elevation closeup of the distal end of the catheter of this invention showing an alternative design of the openings.

FIG. 11 shows a cardiopulmonary system using the catheter of this invention.

FIG. 12 shows positioning the balloon at the distal end of the catheter in the ascending aortic by insertion through the aorta.

FIG. 13 shows positioning the balloon at the distal end of the catheter in the ascending aorta by insertion through the aorta near the subclavian artery.

FIG. 14 shows a flow chart depicting the management of coronary artery disease using this invention.

FIG. 16 shows a phantom view of the venous cannula showing the internal construction of the venous cannula.

FIG. 17 is an enlarged detail drawing showing the construction of the distal tip of the venous cannula.

FIG. 18 is an enlarged proximal end view of the venous cannula.

DETAILED DESCRIPTION OF PRESENTLY PREFERRED EMBODIMENTS

Figure 15:
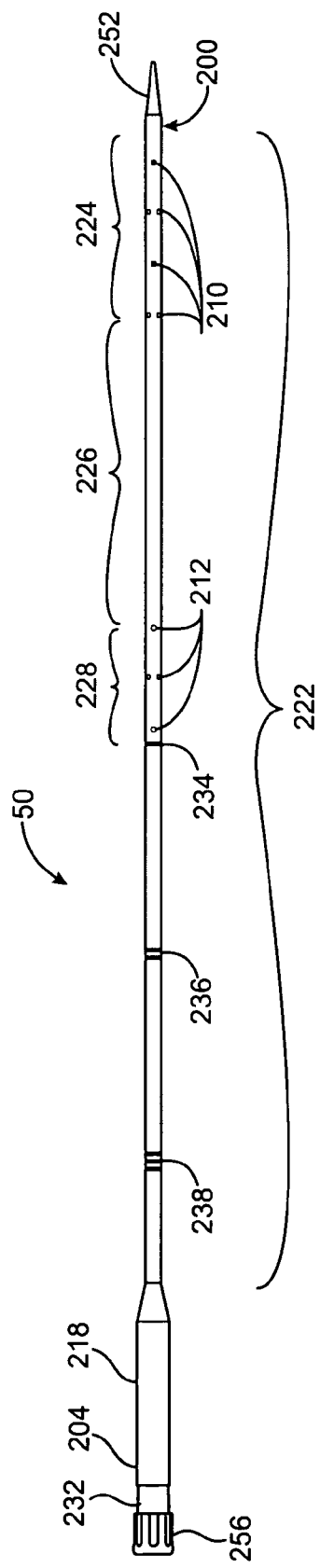
FIG. 15 shows a venous cannula assembly that includes a venous cannula and a dilator/obturator constructed according to the present invention.

The present invention relates to a venous cannula for use in conjunction with cardiovascular examinations, treatments and surgery. The venous cannula is configured for two-stage drainage of oxygen-depleted venous blood from a central venous location via a peripheral venous insertion site, such as a femoral vein. The venous cannula is optimized for use in a cardiopulmonary bypass system that includes a multichannel arterial perfusion catheter. The cardiopulmonary bypass system is advantageous for use in performing standard open chest or least invasive cardiac surgical procedures.

Description of the Multichannel Catheter

In one aspect, this invention includes a multichannel catheter useful in cardiovascular surgery, which allows a physician to deliver extracorporeal blood to a patient undergoing cardiovascular surgery, occlude the flow of blood at the ascending aorta, deliver cardioplegia fluid to the heart and vent the left heart.

The multichannel catheter is of a diameter size to be inserted into the aorta or one of its major branches (e.g. a femoral artery) and used in open chest surgery or in less invasive surgery. Alternatively, the catheter is used in open chest surgery and inserted by cannulation at the aorta or through one of the great arteries, e.g., the brachiocephalic artery. The design of the blood flow configuration will depend on where and how the catheter is to be inserted, as discussed hereinafter.

In general, the multichannel catheter of this invention comprises at least 3 passageways, with a large, central passageway to maximize the flow of oxygenated blood from a cardiopulmonary machine. An important aspect of this invention is to maximize the flow of blood through the large channel while minimizing the outside diameter of the catheter and thus provide adequate systemic extracorporeal blood flow for the vast majority of patients in which the catheter is used. Of the available passage space in the catheter of this invention at least about 70% is allocated to this large passageway to maximize the flow. Preferably about 80% and more preferably about 90% of the available passageway volume, is used for the flow of perfused blood to the arterial side of a patient in need of supplementary, extracorporeal blood circulation. The other channels, at least two, comprise the remainder of the available volume (i.e., about 10%-30%) with each channel integrated into the wall of the large central passageway. Generally, the available volume is determined by calculating the area of a cross-section of each longitudinal passageway and multiplying by the length. Since the length is about the same in each case, the relative volume for each channel will be directly proportional to the cross-sectional area of each passageway.

More specifically, the multichannel catheter has distal and proximal ends and comprises a large central, first channel, i.e., a passageway or lumen. This channel extends substantially the length of the catheter, comprises at least about seventy percent of the available internal channel volume of the catheter, and is closed at its distal end, but has certain outflow openings for extracorporeal blow flow, as discussed in greater detail hereinafter. The catheter has at least second and third channels, each of which extends substantially the length of the catheter, parallel to said first channel but independent thereof. Together, these additional channels comprise not more than about thirty percent of the available internal channel volume of the catheter and are integrated into the wall of the first channel. The second channel (generally the larger of the two smaller channels) is open at its distal end, while the third channel's distal end is in communication with an inflatable means. The catheter further has a plurality of openings near the distal end of said catheter communicating with said first channel and an inflatable means, i.e., a balloon, integrated into the distal end of the catheter between the first channel blood outflow openings and said second channel's distal opening. The openings are said to be "upstream" of the balloon, while the distal opening of the second channel are said to be "downstream" of the balloon. The interior of the inflatable means communicates with the distal end of the third channel through an opening in the wall of the catheter. The catheter is made of physiologically acceptable material and is of a size suitable for insertion into a blood vessel of a mammal, particularly a human. Preferably, at least some and preferably the majority of the plurality of openings communicating with the first channel are elongate in shape with the length of the openings being substantially parallel to the length of the catheter.

Turning now to FIG. 4, one can see a detailed representation of the catheter of this invention which is a cross-sectional view of the length of the catheter. The catheter is shown generally as 30 having a proximal end 31 and a distal end 33. The large first channel 34 is defined by the wall 32 of the catheter. The second channel 36 and the third channel 38 are shown as being integrated into the wall of the first large channel. The second and third channels are integrated with the wall 32 of the first channel 34 and are shown as having an interior wall portion 41 defining the smaller second and third channels.

Toward the distal end 33 of the catheter 30 are located openings 40 that are outlet ports for the fluid passing through the channel 34. In use, that fluid will be blood that is circulated to the arterial side of a patient in need of such extracorporeal circulation. As will be discussed in greater detail, hereinafter, the catheter of this invention is preferably designed to be inserted into a femoral artery of a human patient and advanced sufficiently so that the distal end is positioned in the ascending aorta. Thus, the catheter must be flexible enough to readily bend at its distal end as shown in FIG. 10, but it must also be designed to minimize kinking to avoid reduced fluid flow through the passageways 34, 36 and 38 in FIG. 4. The openings 40 communicating with channel 34 are located on the proximal side (i.e. upstream) of the inflatable means 42 (also referred to as the "balloon") so that blood flows out of channel 34 near the great arteries. While some of the openings may be adjacent the balloon 42, preferably within about an inch of the proximal edge 44 of balloon 42, the openings 40 are located such that they do not contribute to kinking of the catheter as it passes the aortic arch. Thus the openings 40 are located in the distal portion of the catheter so that when the catheter is positioned as shown in FIG. 11 the openings are in a region of the catheter that is relatively straight. A few of the openings may be located immediately adjacent the proximal side of the balloon 42 (e.g., within about an inch of the proximal edge 44 of the balloon 42), while the majority will be proximal to the great arteries.

Alternatively if the catheter is used in open chest surgery, it can be inserted through the aortic arch as shown in FIG. 12 or through the brachiocephalic artery 102 or one of its branches. In FIG. 12, the same numerals are used in describing the catheter of this invention as are used in FIG. 4. Referring now to FIG. 12, the aorta is generally shown as 100 with the ascending aorta 101 and the great arteries shown as 102 (brachiocephalic), 103 (carotid), and 104 (subclavian). In open-chest cardiovascular surgery, the catheter 30 is inserted at the ascending aorta 101 to position balloon 42 snugly against the walls of the ascending aorta 101. In this case, because the catheter 30 does not flex around the aortic arch 105, there is not as much stress on the distal end 33 of catheter 30 and less likelihood of kinking. Thus numerous openings 40 may be located closer to balloon 42 as to insure the flow of blood to the aorta. The same is true of cannulation through one of the great arteries such as the brachiocephalic artery 102 or one of its branches. Another region of insertion may be near the subclavian artery 104 through the aorta as shown in FIG. 13.

Whatever the insertion point of the catheter is, it is important that the total outflow capacity of the outlet ports 40 is greater than the inflow capacity of the blood flowing into the catheter. This will mean that total collective cross-sectional area of openings 40 will exceed the total cross-sectional area of channel 34. Thus, to calculate the collective cross-sectional area of openings 40, one determines the area of each opening and adds the area of each opening. Preferably the total area (i.e. outflow capacity) of the openings will exceed the cross-sectional area (i.e. inflow capacity) of channel 34 by at least a factor of 1.2. Having a factor of greater than about 2 is even more preferable. For example, if the radius of channel 34 is 2.5 mm, the cross-sectional area is 19.6 (2.5.times.2.5.times.3.14=19.6) and the total cross-sectional area of the openings 40 will be at least 23.6 (1.2.times.19.6=23.6), more preferably 39.2 (2.times.19.6=39.2). Preferably, each opening has a cross-sectional area of about 3-40 mm2, preferably about 5 to about 20 mm.sup.2. The total number of openings may be as few as 3 large openings up to about 20 openings of various shapes.

While the shape of the openings 40 may be of any appropriate shape for the outflow of blood, it is preferable that some, generally a majority of the openings are elongate in shape. While the openings may be positioned in any configuration at the distal end of the catheter, for example, the longitudinal axis of the elongate openings may be positioned substantially parallel to the length of the catheter or at a slight angle such that it forms a helical design or the length could be perpendicular to the length of the catheter. However, it is preferred that the elongate openings have the length of the opening substantially parallel to the length of the catheter. The number of openings that can be present may vary from 3 to 20 or more but must be placed in a manner that the structural integrity of the catheter is maintained. By having elongate openings instead of circular openings the sheer stress on the blood is reduced by allowing the blood to flow out of the outlets more easily. In addition to the elongate openings located in the distal region of the catheter other openings may be located further upstream of the elongate openings 40. Further designs may be seen in FIGS. 8, 9 and 10. The design of the openings 40 may generally be that of an oval, a rectangle, a trapezoid or some similar elongated design. In general, they will be approximately one cm to about four cm, preferably about 2.5 cm long with a width at the broadest portion of the opening no more than about 5 mm. The openings 40 are positioned at the distal end of the catheter so that when the catheter is positioned with the balloon 42 in the ascending aorta, the openings are adjacent the great arteries so that blood can flow more freely to the great arteries to ensure the necessary oxygenation of tissues (i.e. perfusion) for the rest of the body. By having a majority of (e.g., oval) openings and ensuring the outflow capacity exceeds the inflow capacity the sheer stress on the blood passing through the first channel 34 will be significantly reduced. By having the elongate openings at the distal end and maximizing the size of channel 34, the flow rate through the large channel 34 may be up to six liters (L) per minute without having adverse affect on the blood due to too much shear stress on the red cells, platelets or white cells. Having the elongate openings and proper outflow capacity also reduces the pressure drop between the proximal end where the catheter is attached to the cardiopulmonary machine and the exit at the openings 40. Generally, the pressure drop will be under 300 millimeters of mercury and preferably under 200 millimeters of mercury. The pressure drop can be further reduced by having additional holes towards the proximal end of the catheter but somewhere between the midpoint of the catheter and the distal end. This design is seen in FIG. 10. As discussed, before the openings 40 will be positioned and constructed to minimize the chance of kinking when the catheter passes over the curve of the aortic arch and generally will be sufficiently proximal of the balloon 42 with the largest cross-section of openings to be positioned in a section of the catheter that remains straight. While, a few (e.g., 2-4) small openings may be placed within about 2.5 cm proximal of the balloon 42, the majority are about 7.5 cm to about 30 cm on the proximal side (i.e., upstream) of the balloon, depending on the catheter sizing for the patient.

In general, the maximum length of the multichannel catheter of this invention will be that length necessary to insert the catheter into the femoral artery of the patient and moving it up the artery to place the distal end having the balloon within the ascending aorta. Depending on the size of the patient, whether a child or an adult, the length may be from about 40 centimeters up to about 100 centimeters or more. Generally, the range will be about sixty to about one hundred centimeters with about eighty-five centimeters being an average length suitable for most people. The length will be significantly less when used in open-chest surgery with aortic insertion or brachiocephalic cannulation.

The outside diameter of the multichannel catheter of this invention will be such that it can be inserted and moved through the femoral artery of the patient and located in the ascending aorta as discussed above. Generally, this will have an outside diameter (OD) of no more than about 30 French, preferably of about 18 to 24 French with about 20 to 22 French outside diameter fitting most patients. The French scale is a scale used for denoting the size of catheters or other tubular instruments, with each unit being roughly equivalent to 0.33 millimeters (mm) in diameter. For example, 18 French indicates a diameter of about 6 millimeters while 20 French would indicate a diameter of about 6.6 millimeters. The thickness of the wall 32 may be between about 0.2 mm to about 1.0 mm. Thus, the inside diameter of channel 34 will generally not exceed about 28.2 French, and may vary from about 14.8-22.5 French.

By using the multichannel catheter of this invention, which is designed to maximize the flow of blood within the large channel while minimizing the outside diameter of the catheter, the peripheral flow of blood to the extremities, i.e., the arms and legs is significantly improved over any known commercial catheter designs. This is thought to be due not only to the improved blood flow through the catheter and out the openings, but also to the smaller outside diameter of the catheter and flow of blood back down the femoral artery around the catheter.

In some cases, it may be preferable to provide the multichannel catheter of this invention with a distal end that has a slight "preshaped" region designed into it. The preshaped region is designed to correlate to the aortic arch. In inserting the catheter the preshaped region is maintained in a relatively straight condition by using a stylet, i.e., a stiff plastic support mechanism positioned in channel 34. This can be used in conjunction with a guide wire positioned in channel 36. When the distal end of the catheter reaches the curve of the aortic arch, the catheter continues to be advanced via the femoral artery, but the stylet is slowly withdrawn allowing the pre-curved region to bend around the aortic arch to have the balloon then located past the brachiocephalic artery but before the coronary ostia.

As shown in the FIG. 4, at the distal end of the catheter of this invention there is located a inflatable means 42 which in general is a balloon that is attached to the distal end of the catheter. The interior of the inflatable means is in fluid communication with the third channel 38 so that the balloon can be inflated or deflated by transporting fluid through the channel to the balloon to inflate it or sucking the fluid out to deflate the balloon. The design of the balloon may be any design known in the art, such as that shown in U.S. Pat. Nos. 5,423, 745; 5,516,336; 5,487,730; and 5,411,479, the pertinent parts of which are incorporated by reference. Other useful balloon components are commercially available to one of ordinary skill. While one balloon is shown in FIGS. 4 and 8-13 multiple balloons could be used, e.g., two. However, for ease of use and preparation, one balloon is preferred. It is also preferred that the distance between the proximal edge 44 of the balloon and the distal side 45 be such that the surface contact with the interior wall of the ascending aorta wall be maximized. This helps ensure a tight seal to prevent leakage. This distance between 44 and 45 may be from about 20 mm to about 50 mm, preferably about 30 mm to about 40 mm.

The second channel 36 is designed to introduce a cardioplegia solution, to evacuate fluid (i.e., vent the left ventricle), or to carry a guidewire or various types of probes or for treating the heart. Thus, it has at least one opening 37 at the distal end 33 of catheter 30 downstream of balloon 42. This allows a cardioplegia solution or the appropriate fiberoptic cable to be inserted into the channel and moved through the channel out exit 37. It also allows for a negative pressure to be applied to vent the left ventricle of the heart.

In a preferred mode of operation, the catheter of this invention is inserted percutaneously or by cutdown into the femoral artery of a patient and is threaded through the femoral artery to the ascending aorta to be positioned there. Occasionally, it may be necessary to supplement the flow of a patient's heart if it has been weakened, and this can be done by flowing oxygenated blood through the central passageway 34 out the outlets 40 to the great arteries and other arteries in the arterial system. If an operation is to be performed on the heart, which requires arrest of the heart, the catheter is positioned appropriately, the balloon is inflated to block the flow of blood into the heart from outflow openings 40. Cardioplegia solution is administered through channel 36 out opening 37 to arrest the heart and blood is circulated through channel 34 out openings 40 to maintain circulation of oxygenated blood in the patient during the operation.

Turning now to FIGS. 5A through 5C and FIG. 6, one can see a cross-sectional view taken along lines 5-5 in FIG. 4. In these figures, it can be seen that the large central passageway 34 is defined by the wall 32 of the overall catheter and that the channels 36 and 38 are integrated into the wall 32. They may be integrated so that they are positioned more interiorly as shown in FIG. 5A or more exteriorly as shown in FIG. 5B with cross-sectional diameters that are essentially a circle. On the other hand, in FIG. 5C, the cross-sectional of channels 36 and 38 may be elongated or oval. While the relative volumes of the two are shown to be about equal, the total volume of flow available for all passageways 34, 36 and 38 is divided as follows. The amount of fluid flowing through passageway 34 will be at least about seventy percent or more (e.g., up to about 90%) in order to achieve the advantages of this invention with the flow through passageways 36 and 38 being the remaining thirty percent or less (i.e., down to about 10%). In general, there will need to be less volume in the channel for communicating with the balloon than in the channel that is available for the cardioplegia or the fiberoptic instruments or cable. While generally, it is preferable to have the channels 36 and 38 opposed one hundred eighty degrees from each other as shown in FIGS. 5A to 5C, it may be possible to have them adjacent as shown in FIG. 6. Having them adjacent makes the preparation a bit more difficult than having them opposed as in FIGS. 5A, 5B and 5C.

The ratio of the total volume of the cardioplegia channel 36 to the balloon inflating channel 38 will vary from about 1:1 to about 4:1. So, for a multichannel catheter in which about 70% of the total available volume is provided for the channel 34 and about 30% of the total available volume is provided for channels 36 and 38, channel 36 will account for about 15% to about 24% with channel 38 accounting for about 15% to about 6%. Alternatively if channels 36 and 38 collectively account for about 10% of the total available volume then channel 36 will have about 5% to about 8% while channel 38 will have about 5% to about 2%.

By referring to FIG. 7, one can see the relative proportions of the three channels of the multi-channel catheter of this invention. In the Figure the abbreviations have the following meanings:
 ID—inner diameter
 OD—outside diameter
 IWT—inner wall thickness
 OWT—outer wall thickness
 Summarizing the dimensions, they are as follows:
 OD 32: 16-30 French (5.3-9.9 mm)
 ID 32: 14.8-28.2 French (4.7-9.3 mm)
 OWT 32: 0.6-1.0 French (0.2-0.3 mm)
 IWT 41: 0.6-1.0 French (0.2-0.3 mm)
 ID 38: 0.6-1.0 French (0.2-0.3 mm)
 ID 36: 0.6-4.0 French (0.2-1.3 mm)

The catheter of this invention is able to handle a blood flow rate through the central channel 34 of about one-half up to about 6 liters per minute with the proper sizing and design. Generally, a flow of about 5 liters per minute is sufficient to handle the vast majority of circulatory needs required by patients having heart surgery performed. On the other hand, the flow of cardioplegia solution or drug-containing solution through channel 36 is generally about 100 to about 300 cubic centimeters (0.1-0.3 liters) per minute. The balloon inflation channel 38, which is generally smaller than channel 36, will be of a size sufficient to carry balloon-inflating fluid, e.g., saline, to the balloon. The volume of the balloon is generally about 40 cc to about 100 cc, generally about 60 cc. Thus, channel 38 is of a size sufficient to carry that volume over a short period of time, i.e., less than a minute and generally less than about 10 seconds. The volume of the balloon will be greater if the distal end of the multichannel catheter is tapered in the region covered by the balloon.

In general, the catheter of this invention will need to be flexible enough to easily be inserted up through the femoral artery to be positioned in the ascending aorta. The flexibility needs to be sufficient so that the catheter can bend but will not kink at body temperature. In general, this flexibility is measured by Durometer and will be somewhere in the 55 to 65 range. Generally, we will have a Durometer reading of about 60. It is preferable that the distal end where the balloon is located is somewhat stiffer than the rest of the catheter. This helps to ensure the positioning of the balloon in the ascending aorta to ensure that it does not get displaced during the operation.

Turning now to FIGS. 8-10, one sees a closeup of the distal end 33 of catheter. It should be understood that the figures are representative, but are not necessarily drawn to scale. This is an external view that show the elongate openings 40 and the balloon 42 in its inflated form, although not fully inflated. In general, the balloon is preferably of an oblong shape as shown in FIG. 8. This maximizes the surface contact with the ascending aorta wall and minimizes the stress on the vessel wall by dispersing the pressure over a greater area. By maximizing the surface contact, the position is maintained to a greater extent. While the surface of the balloon may be smooth, as shown in FIG. 10, it preferably has a design on it that provides additional friction between the balloon surface and the internal surface of the aortic arch. Thus the balloon surface may have either depressions, as shown in FIG. 8, or ridges, as shown in FIG. 9, in a design that helps maintain the balloon in position. It is preferable to have on the surface of the balloon certain ridges or bumps indicated in FIG. 9 as 43 to provide additional friction for maintaining the position of the balloon in place and minimizing the disruption of plaque that may be present. Generally, the volume of the balloon will be about 30 to about 100 cubic centimeters, preferably about 60 cc. The length of the balloon from its proximal end 44 to its distal end 45 will generally be about 2.5 cm to about 7.5 cm with about 4 cm being optimal. It will need to expand sufficiently to block the ascending aorta completely so that blood does not get to the arrested heart from the cardiopulmonary machine.

In performing open heart or least invasive cardiac surgery, generally, it is necessary to do an angiogram by placing an angiogram catheter up the femoral artery and positioning it in the ascending aorta. Based on the length of the angiogram catheter balloon placement position can be determined, the multi-channel catheter of this invention has markings indicating its length measured from the distal end to various distances near the proximal end so that the physician knows exactly how far to insert the catheter of this invention. Having that information indicated on the catheter makes it easier for the physician to do the insertion and also reduces the need to use fluoroscopy to properly insert the catheter. On the other hand, if a angiogram catheter measurement is not done before inserting the catheter of this invention, an ultrasound probe may be used to position the catheter of this invention where the catheter of this invention carries a detectable beam on the tip of the catheter. Alternative methods may be employed for positioning the catheter, such as guidance by fluoroscopy or echocardiography, fiberoptic visualization through the catheter, magnetic or electronic guidance, or other means of insuring proper placement.

The material which is used to manufacture the multichannel catheter of this invention may be any material that is physiologically acceptable, that is it is made of a material that will not have an adverse effect on the patient when used in the manner in which it is intended. Generally this will require the use of biocompatible material (i.e. the body will not react with it) for preparing the catheter of this invention. In addition, the material that is used must possess sufficient stability and flexibility to permit its use in accordance with the process of the invention. Various biocompatible polymers may be used. A polymer that is particularly valuable for preparing the catheter of this invention is polyvinyl chloride (PVC) blood tubing, that has been plasticized. Preferably the plasticizer which is used in the PVC is trioctyl trimellitate (TOTM) while the standard plasticizer di-(2-ethyl hexyl)phthalate (DEHP). TOTM plasticizer is less extractable than DEHP and produces a better blood response. Suitable PVC resin is available from Dow Chemical Corp., Midland, Mich., or Polymer Technology Group (P.T.G.) Inc., Emeryville, Calif. Another polymer that is useful for preparing the multichannel catheter of this invention is medical grade polyurethane. Other polymers may be prepared based on a family of polysiloxane-containing copolymers termed surface modified additions (SMAs). These copolymers may be blended with the base polymer before processing or coated on the blood contacting surface. When blended with the base polymer the SMA will migrate to the polymer surface resulting in a high concentration of the SMA of that surface, which has fewer adverse reactions with the blood that contacts it. When coated, device surfaces are pure SMA. High surface concentration of the SMA are responsible for the improved biocompatibility of extracorporeal circuit components. Plasticized PVC is particularly useful as the base polymer. A further description of these polymers is given in article entitled "Surface Modifying Additives for Improved Device-Blood Compatibility" from ASAR Journal 1994 M619-M624 by Chi-Chun Tsai et al. The article is incorporated herein by reference. Such polymers are available from P.T.G. Corp.

Other useful polymers include polyurethane-urea biomaterials that are segmented polyurethane (SPU) some of which have surface-modifying end groups (SMES) covalently bonded to the base polymer. These are described by Ward, et al. in an article entitled "Development of a New Family of Polyurethaneurea Biomaterials" in Proceedings From the Eighth Cimtec—Forum on New Materials Topical Symposium VIII, Materials in Clinical Applications, Florence, Italy, July, 1994. See also U.S. patent application Ser. No. 08/221, 666, which is incorporated herein by reference.

Sometime the blood interacts with artificial surfaces of polymers in such a way that the blood coagulates on the surface creating thrombi. These thrombi can block the catheter or blood vessels, preventing the blood from flowing and causing oxygen depletion and nutrient starvation of the tissues. Thus the surface of the polymeric material used for the multichannel catheter of this invention should not give rise to thrombus formation. An anti-thrombotic agent can be used to prevent the clots from forming. Some of the blood polymer interactions are discussed in article entitled "Biomaterials in Cardiopulmonary Bypass" found in Perfusion 1994; 9:3-10 by James M. Courtney et al.

Polymer modifications that permit an improvement in blood compatibility while maintaining acceptable levels of other fundamental properties include the treatment of surfaces with protein, the attachment of anti-thrombotic agents and the preparation of biomembrane-mimetic surfaces. The preferred anti-thrombotic agent is the anti-coagulant heparin which can be attached ionically or covalently. Preferably it is attached covalently.

An additional factor to consider in preparing the catheter of this invention is the relative roughness of the blood-contacting surface. Excess surface roughness has deleterious effects on blood flow through the catheter and should be avoided.

Another article that discusses the factors relating to compatibility of surfaces contacting blood is entitled "State-of-the-Art Approaches for Blood Compatibility" from Proceedings of the American Academy of Cardiovascular Perfusion Vol. 13, January 1992, pages 130-132 by Marc E. Voorhees, et al.

Use of the Multichannel Catheter of this Invention

The catheter of this invention may be used in several different ways. For a condition in a patient that needs supplementary extracorporeal blood circulation because of insufficient circulation from his or her own heart, the catheter may be introduced via a femoral artery, positioned as appropriate and attached to a cardiopulmonary bypass machine to circulate blood through the large central channel 34 and out openings 40. When appropriately positioned with the distal end of the catheter in the ascending aorta, a fine fiber optic cable may be threaded through second channel 36 to examine the aortic area of the heart. If it is determined that a heart operation is necessary, the balloon may be inflated through channel 38 to block the ascending aorta, cardioplegia solution may be administered through channel 36 to arrest the heart, and oxygenated blood from a cardiopulmonary machine is pumped through channel 34 and openings 40 into the arterial pathway of the patient's circulatory system. Thus, the device of this invention may be used in cardiovascular surgery in general or various heart examinations or treatments of artery and valvular disease. Cardiovascular surgery is meant to include surgery to the heart or to the vascular system of a patient. The catheter is particularly useful in cardiac surgery, whether open chest surgery or minimally invasive heart surgery. Such surgery may include, but are not limited to, the following:

Coronary artery revascularization such as: (a) transluminated balloon angioplasty, intracoronary stenting or treatment with atherectomy by mechanical means or laser into the coronary arteries via one lumen of the catheter or (b) surgical mobilization of one or both of the mammary arteries with revascularization achieved by distal anastomoses of the internal mammary arteries to coronary arteries via a small thoracotomy.

Any atrial or ventricular septal defect repair such as by (a) "closed" cardioscopic closure or (b) closure as in "open" procedure via a thoracotomy or other limited access incision.

Sinus venosus defect repair similar to above.

Infundibular stenosis relief by cardioscopic techniques.

Pulmonary valvular stenosis relief by cardioscopic techniques.

Mitral valve surgery via thoracotomy.

Aortic stenosis relief by the introduction of instrumentation via a lumen in the aortic catheter into the aortic root.

Left ventricular aneurysm repair via a small left anterior thoracotomy.

A significant advantage of the unique multichannel catheter of this invention is its ability to be adapted to be used in accordance with the needs of a patient. For example, a patient with symptomatic coronary artery disease undergoes a diagnostic evaluation to determine the type of treatment that best suits that patient's condition. As a result of the evaluation, the physician may recommend surgical treatment, interventional cardiology treatment or some alternative treatment. Interventional treatment may include percutaneous transluminal coronary angioplasty, atherectomy or the use of a stent to keep the vessels open. Alternative treatment may include the use of a laser or myoplasty.

If additional treatment is recommended, the multichannel catheter of this invention is particularly valuable in the further evaluation to determine the condition of the patient, the type of treatment recommended and the type of drugs that might be useful to administer to the patient. Thus, in using the multichannel catheter of this invention, the catheter is inserted into a femoral artery by percutaneous puncture or direct cut-dow. The distal end of the catheter, which carries the balloon, is inserted first and moved through the femoral artery to be positioned in the ascending aorta as discussed in more detail hereinafter. Initially, the physician performing the work may wish to introduce instruments through the channel (36 in FIG. 4) or other probes to allow observation or measurement of the internal condition of the artery, aortic arch and/or aortic semilunar valve. A cardioscope, an electrophysiology probe, a transmyocardial revascularization probe, a radiation probe, or the like may also be inserted through channel 36. Once observations are made concerning the condition of the heart and associated arteries, the physician can then take additional steps. For example, it may be desirable to administer a biologically active fluid directly to the heart or aorta using an appropriate liquid composition containing an active entity appropriate for the patient's condition. The active entities in such a biologically active fluid include drugs (particularly those having cardiovascular effect) that are pharmaceutically acceptable small organic molecules, small polypeptide molecules, larger polypeptide molecules, and even a DNA or RNA that may be useful for gene therapy. Examples of useful molecules include those useful as antianginals (e.g., organic nitrates, calcium channel blockers, .beta.-adrenergic antagonists) antihypertensive, antiarrhythmics, antihyperlipoproteinemias, myocardial contractile enhancers, anti-atherosclerotic agents, and the like. Such fluids especially for cardioplegia can best be delivered through channel 36 in FIG. 4, but alternatively can be delivered in the fluid used to inflate balloon 42 through channel 38 in FIG. 4. In the latter case, the material used for the balloon would be semipermeable to allow the drug to diffuse through the balloon membrane. A drug having lipid-dissolving characteristics can be delivered through the balloon membrane. Alternatively, it may be useful to deliver such an active agent by adding it to the cardiopulmonary machine reservoir.

Once the catheter is in place, and observations regarding the internal conditions have been made, the physician then can move on to the next steps. For example, least invasive surgery, as discussed in U.S. Pat. No. 5,452,733, may be performed on a beating heart with no initial cardiopulmonary support, i.e., no blood would flow through the large, central channel, 34 in FIG. 4, but instead the patient's cardiopulmonary system would continue to function. If at any time, the physician would decide that cardiopulmonary support would be needed, supplemental blood flow from a cardiopulmonary (heart/lung) machine could be started and work could be continued with a beating heart or a fibrillating heart. Once a decision is made to completely arrest the heart, cardioplegia solution is delivered to the heart through the channel 36 after balloon 42 is inflated to block the flow of blood to the heart from the cardiopulmonary machine. As described, the multichannel catheter of the invention can be used in least invasive surgical procedures as well as open chest surgery.

The multichannel catheter of this invention is particularly useful in performing heart surgery where the heart is arrested using a cardioplegic solution and blood is circulated to the patient via a cardiopulmonary bypass machine. In this case oxygenated blood is circulated through the large channel of the catheter of this invention. The introduction of negative pressure on the venous drainage system may be used to enhance venous drainage and reduce the need to vent the right side of the heart. Generally, the negative pressure may be maintained at the vena cavae regions (superior and inferior) using a centrifugal pump attached to a standard femoral venous cannula. A system for performing such a process is depicted in FIG. 11.

In general, the process for performing surgery on a mammal's heart comprises a sequence of steps. A single femoral access cannula is inserted into the mammal's femoral vein to position it so the distal open end of the cannula is adjacent the vena cava region of the mammal's heart and the proximal end of the cannula is attached to a cardiopulmonary bypass machine through a centrifugal pump wherein the cardiopulmonary bypass machine comprises a blood oxygenation means fluidly connected to the centrifugal pump. At about the same time a multichannel catheter of this invention is inserted into a femoral artery.

The multichannel catheter is positioned within the subject's blood circulatory system such that the distal end of said catheter is positioned in the ascending aorta such that the first channel openings are located near the great arteries, the inflatable means is located on the cephalid side of the aortic valve and the distal end of the second channel is located proximate the aortic valve and downstream of the inflatable means.

Next, a source of oxygenated blood from the cardiopulmonary machine is connected to the proximal end of said first channel of the catheter and a source of cardioplegia fluid is connected to the proximal end of said second channel. A source of fluid is connected for inflating said inflatable means to the proximal end of said third channel and the inflatable means is inflated to block the flow of blood to the heart.

Cardioplegia solution is pumped into the heart to arrest the mammal's heart and oxygen-rich blood is pumped through said first channel out the first channel openings upstream of the balloon at rate sufficient to maintain the subject's metabolism and perfusion while at the same time oxygen-depleted blood is removed from the mammal's vena cavae regions through the femoral vein cannula by applying a negative pressure using the centrifugal pump. The physician can then perform a surgical operation on the heart as needed and said subject is maintained as needed.

FIG. 11 shows a cardiopulmonary bypass system according to the present invention. A peripheral venous access site, such as the femoral vein, is accessed percutaneously or by cut down using a peripheral access venous cannula 50. In a particularly preferred embodiment of the invention, the cardiopulmonary bypass system utilizes a venous cannula 50 that is optimized for use with the multichannel arterial perfusion catheter, as described below in connection with FIGS. 15-22. This cannula conducts de-oxygenated venous blood from the vena cava 51 to PVC tubing 52 (e.g. 0.5 inch inner diameter). This tubing is attached to the negative pressure (inlet) port 53 of a centrifugal pumping device 54 (such as the St. Jude Medical #2100CP); the positive pressure (outlet) port 55 of the centrifugal pumping device is connected via tubing 56 (0.5 inch ID PVC) to a venous reservoir system 57 (such as the COBE Cardiovascular, Inc. VRB 1800). This configuration pulls blood from the vena cava 51 to the venous reservoir 57. Utilization of negative pressure in this manner to provide venous blood return eliminates the need to "vent" or empty the right heart. By using a centrifugal pump that reaches about −20 to about −50 mm of mercury (mm Hg), a sufficient negative pressure is maintained. The use of a closed reservoir system is preferred to eliminate air/blood interface and associated blood trauma. The venous blood exits the reservoir through tube 58 (e.g. ⅜ inch ID PVC tubing). This tube is connected to an oxygenator/heat exchanger means 59 (such as the COBE Cardiovascular, Inc. model #CML DUO #050-257-000) to oxygenate the oxygen-depleted blood. The blood will be pumped through the membrane/heat exchanger by a roller pump device 60 (such as the COBE Cardiovascular, Inc. model #043-600-000). The oxygenator will oxygenate the blood and the heat exchanger will regulate blood temperature. The oxygenated arterial blood will exit means 59 through tube 61 (such as ⅜ inch ID tubing), pass through an arterial filter 62 (such as a COBE Cardiovascular, Inc. Sentry #020-954-000) and be delivered into the femoral artery via the invention multichannel catheter 63. Preferably, all blood contact components are surface modified to reduce blood trauma, patient inflammatory response and requirements for patient anticoagulation.

The femoral artery catheter 63 provides flow of oxygenated blood to the aorta 64. The invention catheter 63 is introduced into the femoral artery 65 percutaneously or by cut down. The invention catheter 63 is introduced utilizing a guidewire and stylet. The stylet provides stability to the catheter allowing the device to resist kinking during insertion with a minimum required wall thickness of the catheter. Accurate positioning of the balloon will differ from other positioning methods by utilizing measurement of the cardiac catheterization catheter. The appropriate distance will be determined and indicated on the femoral artery catheter 63 prior to insertion; the distance indicator markings 66 will provide simple and accurate balloon positioning. Accurate positioning of the balloon tip may also be enhanced or verified using visualization by transesophogial echo or fluoroscopy.

The invention catheter provides a flow of oxygenated blood to the aorta as part of the cardiopulmonary bypass process. The catheter is of a length sufficient to extend from the insertion point in the femoral artery to the ascending aorta as shown in FIG. 11, which length will vary depending on the size of the patient, as discussed hereinbefore. The catheter has a proximal end 74 and a distal end 75. The catheter has an inflatable balloon 76 located on the proximal side of the distal tip for fixing the catheter within the ascending aorta. A channel extends the length of the catheter to the balloon with an outlet port that communicates with the balloon so that the balloon can be filled with a fluid from a syringe-type inflation device 73 to occlude the ascending aorta as discussed herein. The catheter also has (a) a channel extending from the proximal end 74 to outlet ports 77 upstream of the balloon for delivering oxygenated blood and (b) a channel extending through the entire cannula with an outlet port 78 in the distal tip for a guidewire and/or delivering a cardioplegia solution to the heart through stopcock 68 into inlet port 67 and line 69. Changing the position of the valve in stopcock 68 to connect with line 70 and providing a negative pressure by roller pump 72, allows for the venting of the left ventricle by pulling fluid from the left ventricle through the semilunar valve through opening 78.

Another aspect of this invention may be viewed as an improvement in the process of minimally or "least" invasive heart surgery. For traditional open heart surgery, the surgeon is required to make a long incision in the front of the chest and divide the sternum bone to gain access for the procedure. In minimally invasive heart surgery, a series (4-7) of small incisions are made and the operation is carried out through narrow tubes or ports, using direct or video assisted visualization. Such a minimally invasive process and associated techniques are described in various aspects in U.S. Pat. Nos. 5,433,700; 5,458,574; and 5,452,733, all of which are incorporated by reference in their entirety.

Another aspect of this invention is the overall management of coronary artery disease management using the scheme outlined as follows, in which the multichannel catheter is used in the diagnostic evaluation and ensuing treatment, particularly the surgical treatment. Generally, the management is a combination of preventative care, treatment and follow-up and can be diagrammed as seen in FIG. 14.

How to Make the Multichannel Catheter

Generally the multichannel catheter of this invention is prepared using any technique that provides the multichannel catheter herein described. The key is to ensure that the second and third channels are integrated into the wall of the first channel. This may be done by forming the channels separately then conjoining them, i.e. by gluing or other means. However, the multichannel catheter may be made through a mandrel-dipping technique, or preferably a continuous extrusion process. Extrusion involves forcing a fluid polymer material (as discussed above) through a suitably-shaped die to produce the cross-sectional shape, such as that depicted in FIGS. 5A, 5B, 5C and 6 or other suitable shape as described herein. The extruding force may be exerted by any standard means known in the art such as by a piston or ram or by a rotating screw, which operates within a cylinder in which the polymeric material such as PVC or polyurethane is heated and fluidized. The fluid material is then extruded through the die in a continuous flow. The extrusion head will have a multitubular die to provide a continuous multichannel catheter, essentially as described herein. Using a mandrel-dipping technique, a mandrel having the desired size and cross section design is dipped in or drawn through a fluid polymeric material so that the mandrel is coated with the polymer. The polymer is then dried on the mandrel and removed to give the desired design. This technique may be done at commercial manufacturers, e.g., PTG, Emeryville, Calif. and others.

Once the multichannel catheter is formed, whether by extrusion or mandrel-dipping, it is cut to suitable lengths and treated to provide the further characteristics of the product to make it operable. Such treatment may occur in any particular order. For example, a plurality of openings (40 in FIG. 4) are formed near the distal end of said catheter communicating with said first channel. These openings are made in conformance with the designs discussed herein, and thus are preferably elongate in that the longitudinal axis of the elongate design may be helical or orthogonal, but is preferably substantially parallel to the longitudinal axis of the catheter itself. The openings may be provided by suitably cutting or punching the elongate design into the wall of the catheter. The design is approximately oval, rectangular, or the like with the length of the opening being about a size discussed herein before. The width of the opening will be such it will not weaken the structural integrity of the distal end of the catheter. FIGS. 8, 9 and 10 present various configurations for the positioning of openings 40. Optionally, additional openings communicating with the first channel may be provided along the length of the catheter positioned between approximately the middle of the catheter and the elongate openings near the distal end. The openings are useful in reducing the pressure drop between the proximal end of the catheter and the distal openings to help reduce the sheer stress on the blood.

In addition to the openings that communicate with the first, large channel, at least one opening communicates with the third channel. Thereafter, an inflatable means, i.e. a balloon device, is integrated into the distal end of the catheter such that the interior of the balloon communicates with the outlet of the third channel to allow fluid to flow through the third channel and to the interior of the inflatable means. In general, this may be integrated by positioning a balloon having an opening corresponding to the opening to the third channel and adhering the balloon to the distal end of the catheter between the openings to the first large channel of the catheter and the distal tip of the catheter. This adherence may be performed by using a suitable glue, solvent bond, light sensitive weld, or other suitable means known in the art for this purpose. The material used for the inflatable means may be any suitable biocompatible material that is capable of being inflated and deflated a plurality of times. Polyurethane-based biocompatible polymers are preferred. These are described in the aforementioned article by Ward, et al.

Finally, the distal end of the first, large channel and the third, small channel are closed. This may be achieved by plugging, solvent sealing, heating or other suitable means. The process must be carried out in such a way that the distal end of the second channel remains open.

Having now described in detail how to make and use the catheter of this invention, the following non-limiting example is provided to further explain important concepts of the invention. The example is to be interpreted as representative but not limiting the scope of coverage of this patent application.

All references to any patents or articles in this application are to be interpreted to specially incorporate each in this application by reference.

EXAMPLE 1

This Example shows the importance of the second and third channels, i.e., smaller channels 36 and 38 in the Figures, in the multichannel catheter bearing integrated into the wall of the larger channel and the importance of a significant outflow capacity in the outlet ports to minimize the pressure drop as the flow rate increases through the large channel.

In this test ⅜" inside diameter PVC tubing was used as a channel for standard saline solution. The flow rate through the various tubes was varied from 0.5 to 6 liters per minute. The saline was pumped from a first canister to a second using a roller pump. Tubes 1-6 having slightly different designs were used in the test as follows:

Tube #1: This had two tubes of a much smaller outside diameter, i.e., about ⅛" and about ½2") within the length of large passageway that were not integrate dinto the wall of the ⅜" tube. It had 3 circular outlets of about 2 mm diameter at its distal end adjacent the balloon.

Tube #2: This was similar to #1 except it had 3 slightly larger oval outlets of about 2 mm by about ¾" in. (about 20 mm)

Tube #3: Same design as #2 with 5 additional circular distal outlets of about 2 mm diameter each.

Tube #4: Same design as #2 with 10 additional circular distal outlets of about 2 mm diameter each.

Tube #5: Same design as #2 with 15 additional circular distal outlets of about 2 mm diameter each.

Tube #6: Same design as #1 without the interior tubing.

The pressure drop was measured by pressure manometer gauge prior to the catheter. The saline was pumped through the catheter starting on the proximal end and flowing out the distal end through the outlet ports. Table I shows the results of the test. It clearly shows the importance of not having any interior lines that are not integrated into the wall of the large catheter. The pressure drops at all flow rates are much less for design #6 (more than 50%). Also when the outflow capacity increases the pressure drop decreases, thus placing less stress on the fluid.

TABLE I

| Pressure Drop | | | | | | Flow |
|---|---|---|---|---|---|---|
| #1 | #2 | #3 | #4 | #5 | #6 | Rate |
| 0 | 0 | 0 | 0 | 0 | 0 | .5 |
| 32 | 32 | 30 | 20 | 20 | 21 | 1 |
| 51 | 51 | 51 | 49 | 49 | 30 | 1.5 |
| 74 | 74 | 65 | 65 | 59 | 58 | 2 |
| 109 | 105 | 89 | 89 | 84 | 42 | 2.5 |
| 148 | 140 | 120 | 120 | 110 | 49 | 3 |
| 195 | 190 | 158 | 158 | 147 | 62 | 3.5 |
| 250 | 238 | 192 | 192 | 178 | 82 | 4 |

TABLE I-continued

| Pressure Drop | | | | | | Flow |
|---|---|---|---|---|---|---|
| #1 | #2 | #3 | #4 | #5 | #6 | Rate |
| 300 | 286 | 231 | 231 | 216 | 97 | 4.5 |
| 354 | 335 | 270 | 265 | 251 | 119 | 5 |
| 450 | 430 | 380 | 370 | 350 | 148 | 6 |

The Venous Cannula

FIG. 15 shows a venous cannula assembly that includes a venous cannula 50 and a dilator/obturator 200. The venous cannula 50 has an elongated tubular body 202 that has a proximal end 204 and a distal end 206 with a central lumen 220 extending through the elongated tubular body 202 from the proximal end 204 to the distal end 206. Preferably, the elongated tubular body 202 has an insertion portion 222 that is substantially constant in diameter. In a preferred embodiment, this insertion portion 222 has an external diameter of approximately 17 to 24 French (approximately 5.7 to 8.0 mm external diameter), most preferably approximately 22 French (approximately 7.3 mm external diameter). Optionally, the elongated tubular body 202 has an enlarged diameter proximal extension 218 that facilitates attachment of a proximal fitting 232, which is configured for connecting the venous cannula 50 to a cardiopulmonary bypass machine as illustrated in FIG. 11. Typically, the proximal fitting 232 will be a ⅜ inch or ½ inch barbed fitting. Preferably, there is a smooth, tapered transition 216 between the insertion portion 222 and the enlarged diameter proximal extension 218 to provide smooth laminar blood flow within the central lumen 220.

The venous cannula 50 has an open distal end hole 208 in fluid connection with the central lumen 220 of the elongated tubular body 202. The elongated tubular body 202 also has two groupings of side ports in fluid connection with the central lumen 220. The distal side ports 210 are grouped together over a distal portion 224 of the elongated tubular body 202. Immediately proximal to the distal portion 224 of the elongated tubular body 202 is an imperforate section 226 without any side ports. The proximal side ports 212 are grouped together over a proximal portion 228 of the elongated tubular body 202 immediately proximal to the imperforate section 226. When the venous cannula 50 is inserted into a central venous position via a peripheral venous access site, such as the femoral vein, this configuration positions the distal end hole 208 and distal side ports 210 to withdraw blood from the patient's right auricle and/or superior vena cava and positions the proximal side ports 212 to withdraw blood from the patient's inferior vena cava. The imperforate section 226 between the distal and proximal side ports 210, 212 will allow the surgeon to place a snare around the exterior of the vena cava to isolate the blood flow between the superior and inferior vena cava.

In a particularly preferred embodiment, the venous cannula 50 has sixteen distal side ports 210 arranged in four groups of four distal side ports 210 along the distal 6 to 8 cm of the elongated tubular body 202. Each group of four distal side ports 210 is evenly distributed at approximately 90 degree spacing from one another around the outer circumference of the elongated tubular body 202. The distal side ports 210 of each group of four distal side ports 210 is offset by 45 degrees from each adjacent group of four distal side ports 210. The imperforate section 226 between the distal and proximal side ports 210, 212 is approximately 10-15 cm in length. There are twelve proximal side ports 212 arranged in three groups of four proximal side ports 212 over a distance of approximately 4-6 cm proximal to the imperforate section 226. Each group of four proximal side ports 212 is evenly distributed at approximately 90 degree spacing from one another around the outer circumference of the elongated tubular body 202. The proximal side ports 212 of each group of four proximal side ports 212 is offset by 45 degrees from each adjacent group of four proximal side ports 212.

Preferably, the exterior of the elongated tubular body 202 of the venous cannula 50 is marked with depth markings to aid the surgeon in placement of the venous cannula 50. In the example shown, a first depth marking 234 indicated by a single circumferential stripe is placed approximately 30 cm from the distal end 206 of the elongated tubular body 202, which is just proximal to the proximal side ports 212. A second depth marking 236 indicated by a double circumferential stripe is placed at approximately 40 cm and a third depth marking 238 indicated by a triple circumferential stripe is placed at approximately 50 cm from the distal end 206 of the elongated tubular body 202. The depth markings can be painted or printed on the exterior of the elongated tubular body 202.

FIG. 16 shows a phantom view of the venous cannula 50 showing the internal construction of the venous cannula. FIG. 17 is an enlarged detail drawing showing the construction of the distal tip 206 of the venous cannula 50 and FIG. 18 is an enlarged proximal end view of the venous cannula 50. The elongated tubular body 202 is constructed with a flexible polymer wall 242 reinforced with a wire coil 240, which is preferably made of stainless steel wire. Preferably, the wire coil 240 is completely embedded in the flexible polymer wall 242. The flexible polymer wall 242 may be made by any known process, including extrusion molding, composite lamination or plastisol dip molding of a flexible medical grade polymer. Optionally, the distal tip 206 of the elongated tubular body 202 may be made of a softer polymer than the remainder of the elongated tubular body 202. Acceptable materials for the flexible polymer wall 242 include, but are not limited to, polyvinyl chloride, polyurethane, silicone and polyamide copolymers (e.g. PEBAX). As best seen in FIG. 17, the wire coil 240 may be interrupted for each grouping of side ports 210, 212. Alternatively, the wire coil 240 may be continuous, with the adjacent coils spaced out at appropriate intervals to allow space for placement of the side ports 210, 212. Preferably, the wire coil 240 reinforcement continues through the tapered transition 216 between the insertion portion 222 and the enlarged diameter proximal extension 218 of the elongated tubular body 202, as shown in FIG. 16. Preferably, the wire coil 240 reinforcement continues close to the distal end 206 of the cannula 50, most preferably within 0.25 inches of the tip. The wire coil 240 reinforcement provides hoop strength support to maintain the circular profile of the cannula tip even under acute radius bends of the cannula where otherwise the tip would tend to deform and bow out creating a pocket/ledge between the cannula wall and the obturator 200.

The insertion portion 222 of the elongated tubular body 202 is preferably made with a thin walled construction to maximize the diameter of the central lumen as much as practically possible. By way of example, in a nominally 22 French size venous cannula 50, the insertion portion 222 of the elongated tubular body 202 will have an external diameter of approximately 7.3 mm and an internal diameter of approximately 6.2 mm, with a wall thickness of approximately 0.5 mm. For femoral artery insertion, the insertion portion 222 of the elongated tubular body 202 will preferably have a length of approximately 50-60 cm, plus an optional enlarged diameter proximal extension 218 that adds approximately 10 cm to the overall length of the venous cannula 50. This configuration provides a flow of venous blood that is clinically acceptable for the majority of the patient population without a high degree of hemolysis. A 22 French size venous cannula 50 of this construction provides a flow of venous blood at a flow rate of up to 5 Liters per minute at gravity drainage of 30.0 inches drop with a central venous pressure of 30 mmHg with a mean Hemolytic Index of no greater than 2%.

The dilator/obturator 200 is insertable into the central lumen 220 of the venous cannula 50, as shown in FIG. 15, to block blood flow through the lumen 220 during introduction of the venous cannula 50 into the patient. The distal tip 206 of the elongated tubular body 202 has a smooth, tapered edge and the distal end hole 208 is preferably sized to have a slight interference fit with the body 250 of the dilator/obturator 200. The side ports 210, 212 are preferably circular in shape to facilitate forming by drilling through the flexible polymer wall 242 after molding of the elongated tubular body 202. The side ports 210, 212 will preferably have a diameter of approximately 2-4 mm. Alternatively, the side ports 210, 212 may be formed in other shapes or by other processes. For example, oval side ports can be formed by milling or laser cutting oval holes through the flexible polymer wall 242. All edges of the distal tip 206 and the side ports 210, 212 should have a smooth radius.

Figure 19:
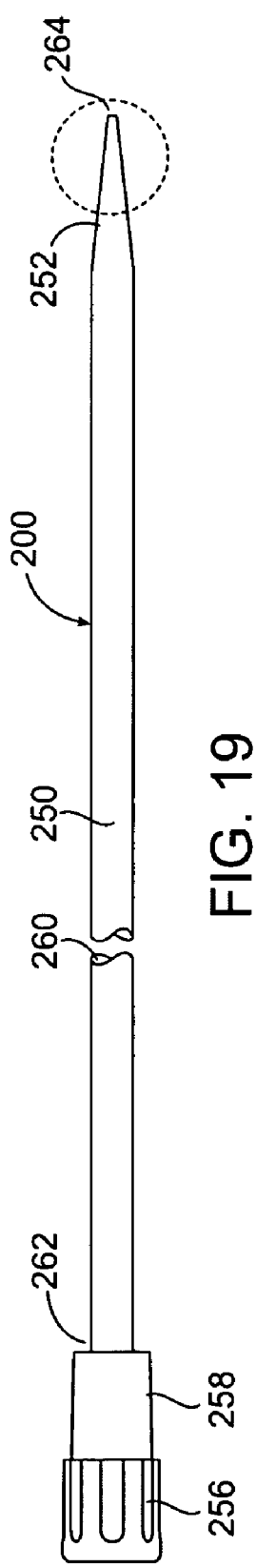
FIG. 19 shows a dilator/obturator for use with the venous cannula.
Figure 21:
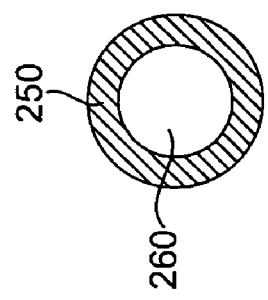
FIG. 21 is an enlarged cross section drawing of the dilator/obturator.
Figure 20:
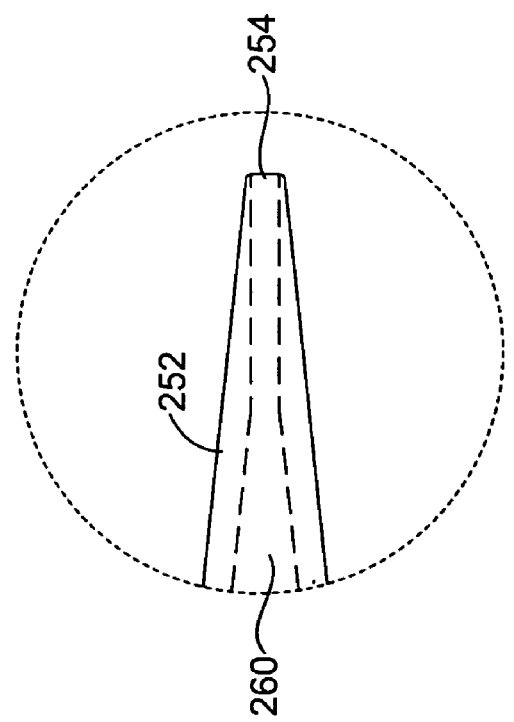
FIG. 20 is an enlarged detail drawing showing the construction of the distal tip of the dilator/obturator.

FIG. 19 shows a dilator/obturator 200 for use with the venous cannula 50. FIG. 20 is an enlarged detail drawing showing the construction of the distal tip of the dilator/obturator and FIG. 21 is an enlarged cross section drawing of the dilator/obturator. The dilator/obturator 200 has an elongated shaft 250 with a proximal end 262 and a distal end 264 and a guidewire lumen 260 extending from the proximal end 262 to the distal end 264. The elongated shaft 250 is typically extrusion molded of a flexible medical grade polymer. Acceptable materials for the elongated shaft 250 include, but are not limited to, polyvinyl chloride, polyurethane (e.g. TECOFLEX), polyethylene, polypropylene and polyamide copolymers (e.g. PEBAX). The elongated shaft 250 of the cannula 50 can be constructed of different materials along its length, with the material at the distal tip 206 being a softer/lower durometer material than remainder of elongated shaft 250. The softer material facilitates forming the tapered profile at the distal tip 206 of the cannula 50 using a necking process, which minimizes any step or ledge between the external diameters of the cannula 50 and obturator 200 when assembled for smooth seamless insertion into the vessel. The external diameter of the elongated shaft 250 is sized to have a sliding fit with the central lumen 220 and a slight interference fit with the distal end hole 208 of the venous catheter 50. For use with the nominal 22 French size venous cannula 500 described above, the elongated shaft 250 will have an external diameter of approximately 5.9 mm. The central lumen 220 is substantially occluded to block blood flow through the lumen 220 during introduction of the venous cannula 50 into the patient. A proximal fitting 256 attached to the proximal end 262 of the elongated shaft 250 has a distal portion 258 that is sized to have a slight interference fit with the proximal connector 232 of the venous cannula 50 to hold the assembly together during insertion into the patient. A tapered distal portion 252 of the elongated shaft 250 facilitates insertion of the dilator/obturator 200 and the venous cannula 50 into a vein at the peripheral venous access site. The guidewire lumen 260 also tapers down at the tapered distal portion 252 to form a distal guidewire port 254 that has a close sliding fit with a selected guidewire, such as a standard 0.038 inch diameter guidewire. The close fit between the guidewire and the distal guidewire port 254 substantially occludes blood flow through the guidewire lumen 260 while a guidewire is inserted through the dilator/obturator 200.

Prior to use, the dilator/obturator 200 is inserted into the venous cannula 50. A peripheral venous access site, such as the femoral artery, is accessed percutaneously with an access needle and a guidewire, or alternatively with a surgical cut down. The access needle is withdrawn and the distal guidewire port 254 is threaded over the guidewire. The tapered distal portion 252 of the dilator/obturator 200 gently dilates the wall of the vein around the needle puncture and provides a smooth transition for the distal tip 206 of the venous cannula 50 to enter the vein. The distal end of the dilator/obturator 200 and venous cannula 50 assembly is then advanced to a central venous location within the right auricle and/or the superior or inferior vena cava. In a preferred method, the distal end hole 208 and the distal side ports 210 of the venous cannula 50 are positioned in the right auricle and the superior vena cava, while the proximal side ports 212 are positioned in the inferior vena cava. Optionally, a snare may be placed around the vena cava in the vicinity of the imperforate section 214 of the elongated tubular body 202 to isolate the superior vena cava from the inferior vena cava. The dilator/obturator 200 is then withdrawn from the venous cannula 50 and the proximal connector 232 is connected to the cardiopulmonary bypass system as described in connection with FIG. 11 above.

Preferably, the venous cannula is supplied sterile to the surgeon in a set that includes a matching dilator/obturator 200, and optionally a guidewire and access needle. Optionally, the venous cannula 50 may be supplied in a complete perfusion set that also includes a multichannel arterial catheter and, optionally, connector tubing for connecting the venous cannula and the multichannel catheter to a cardiopulmonary bypass machine.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

The subject matter claimed is:

1. A cardiopulmonary bypass system comprising:
   a venous cannula configured for withdrawing oxygen-depleted blood from a patient, the venous cannula having an elongated tubular body configured for insertion into a central venous location in the patient via a peripheral venous access site, the elongated tubular body having a proximal end and a distal end and a central lumen extending from the proximal end to the distal end, a proximal connector in fluid connection with the central lumen attached to the proximal end of the elongated tubular body, the proximal connector being configured for connecting to an inlet of a cardiopulmonary bypass machine, a distal end hole in fluid connection with the central lumen, a plurality of distal side ports in fluid connection with the central lumen configured to withdraw blood from the patient's right auricle and/or superior vena cava, a plurality of proximal side ports in fluid connection with the central lumen configured to withdraw blood from the patient's inferior vena cava, the elongated tubular body having an imperforate section separating the distal side ports from the proximal side ports, wherein the venous cannula has sixteen distal side ports arranged in four groups of four distal side ports along the distal portion of the elongated tubular body, each group of four distal side ports being evenly distributed at approximately 90 degree spacing from one another around the outer circumference of the elongated tubular body, the distal side ports of each group of four distal side ports being offset by 45 degrees from each adjacent group of four distal side ports; and wherein the venous cannula has twelve proximal side ports arranged in three groups of four proximal side ports along the proximal portion of the elongated tubular body, each group of four proximal side ports being evenly distributed at approximately 90 degree spacing from one another around the outer circumference of the elongated tubular body, the proximal side ports of each group of four proximal side ports being offset by 45 degrees from each adjacent group of four proximal side ports;
   a multichannel catheter configured for returning oxygen-rich blood to the patient, the multichannel catheter having an elongated catheter body including a first channel defined by a surrounding wall extending substantially the length of the catheter, the first channel being closed at its distal end and having a proximal end configured for connecting to an outlet of a cardiopulmonary bypass machine, a plurality of openings for outflow of blood in the wall of the catheter near the distal end of the catheter and communicating only with the first channel; a second channel extending substantially the length of the catheter parallel to the first channel but independent thereof, the second channel being open at its distal end; a third channel extending substantially the length of the catheter parallel to the first and second channels but independent thereof; and an inflatable member located on the distal end of the catheter between the first channel openings for the outflow of blood and the second channel distal opening and with a distal opening of the third channel in fluid communication with the interior of the inflatable member.

2. The cardiopulmonary bypass system of claim 1 further comprising a cardiopulmonary bypass machine having an inlet in fluid connection with the proximal connector of the venous cannula and an outlet in fluid connection with the first channel of the multichannel catheter.

3. The cardiopulmonary bypass system of claim 1 further comprising a dilator/obturator configured for insertion into the central lumen of the venous cannula, the dilator/obturator having a tapered distal portion to facilitate insertion of the dilator/obturator and the venous cannula into a vein at the peripheral venous access site.

4. The cardiopulmonary bypass system of claim 1 wherein the dilator/obturator has an elongated shaft with a proximal end and a distal end and a guidewire lumen extending from the proximal end to the distal end.

5. The cardiopulmonary bypass system of claim 1 wherein the venous cannula has a plurality of approximately circular distal side ports grouped together along a distal portion of the elongated tubular body and a plurality of approximately circular proximal side ports grouped together along a proximal portion of the elongated tubular body.

6. The cardiopulmonary bypass system of claim 1 wherein the elongated tubular body of the venous cannula is constructed with a coiled reinforced wall surrounding the central lumen.

7. The cardiopulmonary bypass system of claim 1 wherein the elongated tubular body of the venous cannula is constructed with different materials along the length of the elongated tubular body, with a distal tip portion of the elongated tubular body being made of a softer material than the remainder of the elongated tubular body.

8. The cardiopulmonary bypass system of claim 1 wherein the elongated tubular body of the venous cannula is configured with depth markings along the length of the elongated tubular body to facilitate insertion of the venous cannula of a patient.

9. A method of performing cardiopulmonary support on a patient comprising:

- inserting a venous cannula into a central venous location in the patient via a peripheral venous access site, the venous cannula having an elongated tubular body having a proximal end and a distal end and a central lumen extending from the proximal end to the distal end, a proximal connector in fluid connection with the central lumen attached to the proximal end of the elongated tubular body, a distal end hole in fluid connection with the central lumen, wherein the venous cannula has sixteen distal side ports arranged in four groups of four distal side ports along the distal portion of the elongated tubular body, each group of four distal side ports being evenly distributed at approximately 90 degree spacing from one another around the outer circumference of the elongated tubular body, the distal side ports of each group of four distal side ports being offset by 45 degrees from each adjacent group of four distal side ports; and wherein the venous cannula has twelve proximal side ports arranged in three groups of four proximal side ports along the proximal portion of the elongated tubular body, each group of four proximal side ports being evenly distributed at approximately 90 degree spacing from one another around the outer circumference of the elongated tubular body, the proximal side ports of each group of four proximal side ports being offset by 45 degrees from each adjacent group of four proximal side ports;
- positioning a plurality of distal side ports in fluid connection with the central lumen to withdraw blood from the patient's right auricle and/or superior vena cava, positioning a plurality of proximal side ports in fluid connection with the central lumen to withdraw blood from the patient's inferior vena cava, the elongated tubular body having an imperforate section separating the distal side ports from the proximal side ports;
- inserting a multichannel catheter into the patient's aorta, the multichannel catheter having an elongated catheter body including a first channel defined by a surrounding wall extending substantially the length of the catheter, the first channel being closed at its distal end and having a proximal end configured for connecting to an outlet of a cardiopulmonary bypass machine, a plurality of openings for outflow of blood in the wall of the catheter near the distal end of the catheter and communicating only with the first channel; a second channel extending substantially the length of the catheter parallel to the first channel but independent thereof, the second channel being open at its distal end; a third channel extending substantially the length of the catheter parallel to the first and second channels but independent thereof;
- occluding the patient's aorta by inflating an inflatable member located on the distal end of the catheter between the first channel openings for the outflow of blood and the second channel distal opening, a distal opening of the third channel being in fluid communication with the interior of the inflatable means;
- connecting the proximal connector of the venous cannula to an inlet of a cardiopulmonary bypass machine;
- connecting the proximal end of the multichannel catheter to an outlet of the cardiopulmonary bypass machine; withdrawing oxygen-depleted blood from the patient through the venous cannula;
- oxygenating the oxygen-depleted blood with the cardiopulmonary bypass machine; and
- returning oxygen-rich blood to the patient through the first channel of the multichannel catheter.

10. The method of claim 9 further comprising:

- inserting a dilator/obturator into the central lumen of the venous cannula prior to inserting the venous cannula into the patient, the dilator/obturator having a tapered distal portion to facilitate insertion of the dilator/obturator and the venous cannula into a vein at the peripheral venous access site; and
- withdrawing the dilator/obturator from the central lumen of the venous cannula prior to connecting the proximal connector of the venous cannula to the inlet of the cardiopulmonary bypass machine.

* * * * *